US 9,416,358 B2

(12) United States Patent
Mizuno et al.

(10) Patent No.: US 9,416,358 B2
(45) Date of Patent: Aug. 16, 2016

(54) METHOD FOR EXCLUSIVE SELECTION OF CIRCULARIZED DNA FROM MONOMOLECULAR DNA IN CIRCULARIZING DNA MOLECULES

(75) Inventors: Shinichi Mizuno, Kurume (JP); Hidetoshi Ozawa, Kurume (JP); Koji Nagafuji, Kasuga (JP); Takashi Okamura, Fukuoka (JP)

(73) Assignee: KURUME UNIVERSITY, Fukuoka (JP)

( * ) Notice: Subject to any disclaimer, the term of this patent is extended or adjusted under 35 U.S.C. 154(b) by 55 days.

(21) Appl. No.: 14/240,488

(22) PCT Filed: Aug. 24, 2012

(86) PCT No.: PCT/JP2012/071492
§ 371 (c)(1),
(2), (4) Date: Feb. 24, 2014

(87) PCT Pub. No.: WO2013/031700
PCT Pub. Date: Mar. 7, 2013

(65) Prior Publication Data
US 2014/0303004 A1 Oct. 9, 2014

(30) Foreign Application Priority Data
Aug. 31, 2011 (JP) .................................. 2011-189280

(51) Int. Cl.
*C12N 15/10* (2006.01)
*C07H 21/04* (2006.01)
(Continued)

(52) U.S. Cl.
CPC ............ *C12N 15/1065* (2013.01); *C07H 21/04* (2013.01); *C12N 15/10* (2013.01);
(Continued)

(58) Field of Classification Search
CPC ........... C12N 15/1065; C12N 15/1096; C12N 15/1003; C12N 15/10; C12N 15/64; C12Q 1/6883; C12Q 1/6809; C12Q 1/6806; C07H 21/04
See application file for complete search history.

(56) References Cited

U.S. PATENT DOCUMENTS 8,352,194 B1   1/2013 Blanck
2006/0292611 A1 12/2006 Berka et al.
(Continued)

FOREIGN PATENT DOCUMENTS

JP   2008-504805   2/2008
JP   2008-295444   12/2008
(Continued)

OTHER PUBLICATIONS pUC19 map—NEB 2011.*
(Continued)

*Primary Examiner* — Jeremy C Flinders
(74) *Attorney, Agent, or Firm* — Wenderoth, Lind & Ponack, L.L.P.

(57) ABSTRACT

The present invention provides a method for producing a circular DNA molecule having a specific structure that enables to distinguish circular DNA formed from a single DNA molecule (single-molecule circular DNA), from circular DNA formed from multiple DNA molecules (multiple-molecule circular DNA) and also from single-molecule circular DNA derived from the circular DNA formed from multiple DNA molecules. According to the present invention, only single-molecule circular DNA that is not derived from multiple-molecule circular DNA can be selected in the production of circular DNA.

5 Claims, 9 Drawing Sheets

(51) Int. Cl.
  *C12Q 1/68* (2006.01)
  *C12N 15/64* (2006.01)
  *C12N 9/00* (2006.01)

(52) U.S. Cl.
  CPC .............. *C12N 15/64* (2013.01); *C12Q 1/6806* (2013.01); *C12N 9/93* (2013.01); *C12N 15/1003* (2013.01); *C12N 15/1096* (2013.01); *C12Q 1/6809* (2013.01); *C12Q 1/6883* (2013.01); *C12Q 2521/301* (2013.01); *C12Q 2525/307* (2013.01)

(56) References Cited

U.S. PATENT DOCUMENTS

| | | |
|---|---|---|
| 2008/0090776 A1 | 4/2008 | Mano et al. |
| 2009/0176652 A1 | 7/2009 | Dahl et al. |
| 2012/0202214 A1 | 8/2012 | Omi |
| 2013/0102006 A1 | 4/2013 | Takeuchi et al. |
| 2013/0164757 A1 | 6/2013 | Mizuno et al. |

FOREIGN PATENT DOCUMENTS

| | | |
|---|---|---|
| JP | 2008-545448 | 12/2008 |
| JP | 2011-510669 | 4/2011 |
| WO | 2006/003721 | 1/2006 |
| WO | 2009/032167 | 3/2009 |
| WO | 2009/098037 | 8/2009 |
| WO | 2011/043220 | 4/2011 |
| WO | 2011/103236 | 8/2011 |
| WO | 2011/162295 | 12/2011 |
| WO | 2012/014795 | 2/2012 |
| WO | 2012/029577 | 3/2012 |
| WO | 2013/006195 | 1/2013 |
| WO | 2013/018882 | 2/2013 |

OTHER PUBLICATIONS

Linearized pUC19—Clontech 2010.*
International Preliminary Report on Patentability and Written Opinion of the International Searching Authority issued Mar. 14, 2013 in International Application (PCT) No. PCT/JP2011/068856.
International Search Report issued Nov. 22, 2011 in International Application (PCT) No. PCT/JP2011/068856.
United States Office Action issued Mar. 25, 2014 in U.S. Appl. No. 13/819,396.
Supplementary European Search Report issued Jan. 22, 2014 in European Application No. 11821594.6.
Melissa J. Fullwood, et al., "Next-Generation DNA Sequencing of Paired-End Tags (PET) for Transcriptome and Genome Analyses", Genome Research, vol. 19, No. 4, Apr. 1, 2009, pp. 521-532.
"Preparing 2-5kb Samples for Mate Pair Library Sequencing", Illumina, Feb. 2009.
Michael L. Metzker, "Sequencing Technologies—The Next Generation", Nature Reviews Genetics, vol. 11, No. 1, Jan. 1, 2010, pp. 31-46.
Bashir et al., "Evaluation of Paired-End Sequencing Strategies for Detection of Genome Rearrangements in Cancer", Plos Computational Biology, Apr. 2008, vol. 4, No. 4, e1000051.
International Preliminary Report on Patentability issued Mar. 4, 2014 in corresponding International Application No. PCT/JP2012/071492.
Mitelman et al., "Fusion genes and rearranged genes as a linear function of chromosome aberrations in cancer", Nature Genetics, Apr. 2004, vol. 36, No. 4, pp. 331-334.
Ruan et al., "Multiplex parallel pair-end-ditag sequencing approaches in system biology", Wires System Biology and Medicine, Mar./Apr. 2010, vol. 2, pp. 224-234.
Soda et al., "Identification of the transforming *EML4-ALK* fusion gene in non-small-cell lung cancer", Nature, Aug. 2007, vol. 448, pp. 561-566.
Tomlins et al., "Recurrent Fusion of *TMPRSS2* and ETS Transcription Factor Genes in Prostate Cancer", Science, Oct. 2005, vol. 310, pp. 644-648.
European Office Action dated Mar. 8, 2016 issued in corresponding European Patent Application No. 11821594.6.
European Office Action dated Mar. 8, 2016 issued in corresponding European Patent Application No. 12827670.6.
U.S. Office Action dated Feb. 26, 2016, issued in corresponding U.S. Appl. No. 14/594,458.

* cited by examiner

Figure 9

METHOD FOR EXCLUSIVE SELECTION OF CIRCULARIZED DNA FROM MONOMOLECULAR DNA IN CIRCULARIZING DNA MOLECULES

TECHNICAL FIELD

The present invention relates to: a method for producing a circular DNA molecule having a structure that enables to distinguish circular DNA formed from a single DNA molecule, from circular DNA formed from multiple DNA molecules and also from circular DNA derived from the circular DNA formed from multiple DNA molecules; a method for selecting only circular DNA formed from a single DNA molecule; a novel adapter used for such methods; and a kit for producing a circular DNA, comprising the novel adapter. The present invention further relates to a method for identifying and/or detecting a gene using circular DNA produced by the above-mentioned method. In particular, the invention relates to a method for identifying and/or detecting a fusion gene that causes various pathologic conditions.

BACKGROUND ART

Vector method is a conventional gene analysis method. In the vector method, a target gene to be analyzed is incorporated into a vector, and the full-length sequence of the gene obtained after the proliferation is then determined using a sequencer. However, the vector method is problematic in that it needs a culture operation, and also in that a sequencer should be used to analyze the full length of a gene.

In recent years, a high speed sequencer used in gene analysis has been developed, and with the development of this sequencer, mate-pair method as a gene analysis means has attracted attention.

FIG. 1 schematically shows the outline of gene analysis using the mate-pair method. In the mate-pair method, a nucleotide sequence for ligation (a restriction enzyme recognition site) is attached to the both ends of the target gene to be analyzed, and the target gene is then circularized. Then, a part including 15 nucleotides or more, and preferably 25 nucleotides or more to several tens of nucleotides or less, of both sides flanking to the restriction enzyme recognition site is cleaved from the circularized gene, generally using a type II restriction enzyme. The part is amplified by PCR, and the nucleotide sequence of the cleaved partial gene is then determined. Thereby, the sequences of both ends of the target gene are determined, and the target gene can be then identified using known sequence data. Mate pair means the sequence data of a pair of nucleotide sequences obtained by reading both ends of a single DNA fragment.

Practically used methods of cleaving a given number of nucleotides from a gene include: a method of cutting sites apart from the recognition site using a type II restriction enzyme to cleave a given number of nucleotides out; and a method comprising physically cutting circular DNA using sonication or the like, recovering a cleaved fragment with biotin attached to the linker, then amplifying the fragment by PCR, and then determining the sequence of the amplified PCR product.

The mate-pair method can, therefore, identify a known gene by reading a certain length of nucleotide sequence including the both sides flanking to the ligation site in a gene circularized by ligating the both ends of the DNA. Basically, when partial nucleotide sequences of the head and tail portions of a gene were read, these sequences would allow a reliable discrimination among individual genes. Accordingly, the mate-pair method has been adopted as a reliable and simple gene analysis method (Non Patent Documents 1 and 2). Moreover, the mate-pair method has been applied to the next generation sequence analysis, and thus it has become increasingly important together with the emergence of a high speed sequencer.

However, when a DNA is circularized for gene analysis according to the mate-pair method, besides the self-circularization of a single gene or a single DNA (a single molecule), the circularization of a plurality of DNAs (a plurality of molecules) and the linear binding of a plurality of molecules (two or more molecules) also take place. A linear molecule consisting of a plurality of molecules can be separated and eliminated from a circular molecule by the subsequent operations. On the other hand, a circular molecule consisting of a plurality of molecules cannot be separated from a circular molecule consisting of a single molecule, and it becomes a contaminant. A circular product consisting of a plurality of molecules inhibits individual gene analyses and significantly decreases analytical specificity for the following reasons. Specifically, as shown in FIG. 2, when three types of cDNAs are to be self-circularized, when only single-molecule DNA is circularized as shown in (B), a gene can be specified using precise sequences according to the mate-pair method. However, other than the circularization of a single molecule as shown in (B), an uncircularized linear product may be generated as shown in (C), or two or more cDNAs may be circularized as shown in (D). In the case of (C), the linear product can be eliminated with DNA exonuclease. However, in the case of (D), a circularized product consisting of a plurality of cDNAs is recognized as a circularized molecule, and thus, it cannot be eliminated and becomes a contaminant in the gene analysis according to the mate-pair method.

The gene analysis according to the mate-pair method intends to identify a target gene based on the nucleotide sequences of both ends of the target gene. Specifically, a ligation adapter for circularization is attached to both ends of individual genes, and the two adapter sites are then ligated to each other to circularize the gene. Then, a part including a certain number of nucleotides at both sides with the adapter site being the center is cleaved from the gene. Consequently, the gene can be identified by analyzing the nucleotide sequence of a portion from each end of the original gene. Hence, a circularized product of a plurality of molecules has a plurality of adapter sites, and the two ends attached to an adapter are ends of different genes. When gene analysis is carried out, a circularized product is cleaved according to either one of the above described two methods, such that parts including nucleotide sequences of a certain number of nucleotides of the both ends attached to the adapter, with the adapter being the center, can be obtained, as described above. Accordingly, the gene fragment for the analysis obtained from circularized products of a plurality of molecules comprises ends of different genes. Thus, the analysis of a single gene cannot be carried out. As such, in the gene analysis according to the mate-pair method, the presence of a circularized product of a plurality of molecules inhibits each gene analysis.

The probability of circularization of a plurality of DNA molecules generally ranges from few to dozen percent, depending on the method applied. In the analysis of a known gene, they are recognized as abnormal nucleotide sequences and thus, elimination of them from the sequence to be analyzed is usually possible. Hence, it causes only a slight decrease in accuracy, although the operation becomes complicated. However, in a case in which the mate-pair method is used to detect the presence of an abnormal gene, such as a fusion gene, in a group of normal genes, when a plurality of normal genes are circularized, it is determined that abnormal genes are present. As a result, it becomes impossible to accurately confirm the presence of an abnormal gene such as a fusion gene.

The fusion gene is a gene with a novel function that is constructed by binding a plurality of (two) genes to each other. For example, abnormalities in chromosome structure, such as deletion, overlapping, recombination and translocation, are found in a cancer cell. When the cleavage and ligation of a gene occur at a DNA level and a structural gene is present at each cleavage point, a fusion gene is formed.

In general, a fusion gene is lethal or senseless to cells, and it does not cause clinical problems in many cases. However, when cell growth is abnormally promoted as a result that a fusion protein generated from such a fusion gene inhibits the control of the cell growth, it causes clinical problems such as tumor formation.

It had been considered that the fusion gene is mainly expressed in hematopoietic tumors. In recent years, however, it has been expected that the fusion gene would be also associated with epithelial solid tumors (Non Patent Document 3). Among such solid cancers, responsible fusion genes have been discovered from prostatic cancer and lung cancer (Non Patent Documents 4 and 5).

From these findings, the analysis of a fusion gene, namely, confirmation of the presence of a fusion gene, has attracted attention as a novel method for diagnosing tumors (cancers) and the like. Specifically, by detecting a known fusion gene that has been known as corresponding to pathologic conditions, it becomes possible to make a rapid diagnosis of the pathologic conditions. Furthermore, the discovery of a novel fusion gene leads to the discovery of drug discovery targets.

On the other hand, conventional chromosome analyses performed on solid tumors had had a certain limit, and it had been extremely difficult to analyze and/or confirm a fusion gene. Recently, novel methods, such as the cDNA functional expression analysis method according to Mano et al., have been developed. However, these techniques have been still insufficient in terms of complicated operations, problems regarding accuracy, etc. (Patent Document 1). In addition, various types of next-generation high speed gene sequencers have been recently developed. Thus, high speed sequence analysis of genes has significantly progressed, and gene analysis in a short time has been realizing. Hence, searching for fusion genes have been started according to high-speed and/or high-scale nucleotide sequence analysis of tumor genomes and/or genes (Non Patent Document 6).

In order to identify a fusion gene by sequence analysis using the mate-pair method, it is essential to reliably obtain circular DNA formed from a single cDNA molecule. A schematic view of the analysis of a fusion gene according to the mate-pair method is shown in FIG. 3. There is a case, however, in which single circular DNA may be formed from a plurality of cDNA molecules, as shown in FIG. 4. Thus, when sequence analysis is carried out according to the mate-pair method, the result that a normal gene appears as a fusion gene may be obtained. When this gene is eliminated for the reason that it is not present in a conventional gene sequence, a fusion gene is also eliminated. As a result, it becomes substantially impossible to confirm the presence of a fusion gene.

When a fusion gene is to be detected by the sequence analysis according to the mate-pair method, it is essential to eliminate circularized cDNA of a plurality of genes.

To date, the present inventors have found a method for causing only circularization of a single DNA molecule while not causing intermolecular circularization of multiple DNA molecules, by performing two-step ligation using an adapter having a specific structure (not published). However, even by this method, it has been impossible to completely prevent circularization of multiple DNA molecules and to eliminate circular DNA formed from multiple DNA molecules at a probability of 100%. In an analysis using the mate-pair method, and in particular, in an analysis performed for the purpose of searching for a novel fusion gene, when only a little amount of circularized DNA formed from multiple genes is present, it would become pseudo-positive clones. Thus, it is problematic.

Accordingly, it has been desired to develop a method for reliably obtaining only circular DNA formed from a single DNA molecule, while completely eliminating circular DNA formed from multiple DNA molecules.

CITATION LIST

Patent Document

Patent Document 1: Japanese Patent No. 4303303

Non Patent Document

Non Patent Document 1: *Tanpakushitsu Kakusan Koso*, August 2009, (1233-1247, 1271-1275)
Non Patent Document 2: "Shikkan Idenshi no Tansaku to Chokosoku Sequence," *Jikken Igaku* extra edition, Vol. 27, No. 12 (2009, 113 (1929)-143 (1959))
Non Patent Document 3: Mitelman et al., 2004, Nature Genetics, Vol. 36, No. 4, pp. 331-334
Non Patent Document 4: Chinnaiyan et al., 2005, Science, Vol. 310, pp. 644-648
Non Patent Document 5: Soda et al., 2007, Nature, Vol. 448, pp. 561-566
Non Patent Document 6: Bashir et al., April 2008, PLoS Computational Biology, Vol. 4, Issue 4, e1000051

SUMMARY OF INVENTION

Technical Problem

It is an object of the present invention to provide: a method for producing a circular DNA molecule having a specific structure that enables to distinguish circular DNA formed from a single DNA molecule (hereinafter also referred to as "single-molecule circular DNA"), from circular DNA formed from multiple DNA molecules (hereinafter also referred to as "multiple-molecule circular DNA") and also from single-molecule circular DNA derived from the multiple-molecule circular DNA; and a method for selecting only single-molecule circular DNA that is not derived from multiple-molecule circular DNA in the production of circular DNA.

Solution to Problem

The present inventors have found that it becomes possible to produce a circular DNA molecule having a specific structure that enables to distinguish single-molecule circular DNA that is not derived from multiple-molecule circular DNA, from multiple-molecule circular DNA and also from single-molecule circular DNA derived from the multiple-molecule circular DNA, by introducing adapters having specific structures each comprising unique sequences into a single DNA molecule and then performing two-step cleavage and ligation. The inventors have found a method for selecting only single-molecule circular DNA that is not derived from multiple-molecule circular DNA by determining the sequences of the adapter sites after production of the circular DNA molecule having the aforementioned structure.

Definition

In the present description, the "single-molecule circular DNA" means circular DNA formed from a single DNA molecule, and the "multiple-molecule circular DNA" means circular DNA formed from multiple DNA molecules.

In the present description, the term "circular DNA molecule" means a single circular DNA molecule or multiple circular DNA molecules. In addition, the multiple circular DNA molecules may also be referred to as a "group of circular DNA molecules" consisting of multiple circular DNA molecules having identical or different sequences.

In the present description, with regard to a DNA molecule, the description "derived from XX" is used to mean that a certain treatment is performed on the DNA molecule XX, and that as a result, the aforementioned DNA molecule is generated from the DNA molecule XX. This phrase does not mean that a novel molecule is generated, but it typically means that a portion is separated from a DNA molecule and it becomes an independent DNA molecule, or that a portion of a DNA molecule is cleaved and thereby, a molecule that is shorter than the molecule before cleavage is generated, or the like.

For example, single-molecule circular DNA that is "derived from" multiple-molecule circular DNA means circular DNA formed from a single DNA molecule, wherein the circular DNA is formed by self-circularization of a single linear DNA molecule generated as a result of cleaving multiple-molecule circular DNA by a treatment with restriction enzymes or the like.

On the other hand, single-molecule circular DNA that is "not derived from" multiple-molecule circular DNA means circular DNA formed from a single DNA molecule, wherein the circular DNA is generated as a result of self-circularization of a single linear DNA molecule without the formation of multiple-molecule circular DNA.

Moreover, the cleavage end that is "derived from" the adapter (A) or (b) means an end generated as a result of cleaving the cleavage site of the adapter (A) or (b). For example, a 5' or 3' protruding end generated as a result of a restriction enzyme treatment corresponds to this cleavage end.

In the present description, the "unique sequence" means a unique sequence for each adapter (b), which is different depending on each adapter (b). When the type of such unique sequences (i.e. the type of adapters (b)) is sufficiently increased, the adapters (b) having different unique sequences each bind to different DNAs of interest. Thereby, in the method of the present invention, using such a unique sequence as a mark, it becomes possible to determine whether the produced circular DNA molecule is single-molecule circular DNA that is not derived from multiple-molecule circular DNA, or it is multiple-molecule circular DNA or single-molecule circular DNA derived from the multiple-molecule circular DNA.

In the present description, the phrase "'select' only single-molecule circular DNA that is not derived from multiple-molecule circular DNA" may be used to mean that single-molecule circular DNA that is not derived from multiple-molecule circular DNA is physically separated from a group of circular DNA molecules, or it may also be used to mean that only information obtained from single-molecule circular DNA that is not derived from multiple-molecule circular DNA is selected at a stage of data analysis from among information obtained from a group of circular DNA molecules (e.g. nucleotide sequence data).

In the present description, the term "palindromic restriction enzyme site" is used to mean the recognition site of restriction enzyme that recognizes a palindromic sequence, and the term "non-palindromic restriction enzyme site" is used to mean the recognition site of restriction enzyme that recognizes a non-palindromic sequence.

In a first embodiment, the present invention provides a method for producing a group of circular DNA molecules, the method comprising the following steps, wherein the method enables to select only single-molecule circular DNA that is not derived from multiple-molecule circular DNA from a group of circular DNA molecules produced by the method:

1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the adapter (b) side, such that the adapter (A) in the adapter (B) is located outside of the bond of the DNA molecule to the adapter (b), wherein the adapter (A) comprises a cleavage site generating a cleavage end non-specifically binding to all of the cleavage ends of the adapter (A), and the adapter (b) comprises two unique sequences different depending on each adapter (b), wherein the two unique sequences are identical in sequence and oriented in the same direction or reversely to each other; and between the two unique sequences, the adapter (b) also comprises a cleavage site generating a cleavage end non-specifically binding to all of the cleavage ends of the adapters (b), wherein the cleavage site generates a cleavage end that is not cleaved upon cleaving the cleavage site of the adapter (A) and does not bind to the cleavage end of the adapter (A);

2) a first cleavage step of cleaving the DNA molecule obtained in step 1) at the cleavage site of the adapter (A);

3) a first circularization step of binding both ends of the DNA molecule obtained in step 2) to circularize the DNA molecule;

4) a step of eliminating an uncircularized linear DNA molecule in step 3);

5) a second cleavage step of cleaving the circular DNA molecule obtained in step 3) and step 4) at the cleavage site of the adapter (b); and 6) a second circularization step of binding both ends of the DNA molecule obtained in step 5) to circularize the DNA molecule;

wherein the circular DNA molecule obtained in step 6) is determined to be single-molecule circular DNA that is not derived from multiple-molecule circular DNA, when two unique sequences contained in an adapter (b) portion are identical to each other as a result of determination of the sequence of the adapter (b) portion, and the circular DNA molecule obtained in step 6) is determined to be multiple-molecule circular DNA or single-molecule circular DNA derived from the multiple-molecule circular DNA, when the two unique sequences are different from each other.

It is to be noted that the following types of DNAs may remain as linear DNAs after completion of step 6): single-molecule DNA (a trace amount), which has failed to rebind the portion (b) cleaved in step 5); and single-molecule or multiple-molecule DNAs (a major amount of the linear DNAs), which have been circularized with a plurality of DNA molecules in step 3) and have failed to rebind each adapter (b) after the cleavage of the adapter in step 5). These linear DNAs may be eliminated, but may not be necessarily eliminated. This is because these DNAs do not have a structure in which two identical unique sequences are aligned, and thus, they can be distinguished by determining the sequence of the adapter (b) portion and can be eliminated from analysis targets.

Moreover, in a second embodiment, the present invention provides a method for producing a single-molecule circular DNA that is not derived from multiple-molecule circular DNA, the method comprising the following steps:

1) a step of producing a circular DNA molecule by the method of the first embodiment of the present invention; and 2) a step of determining the sequence of an adapter (b) portion in the produced circular DNA molecules and selecting only single-molecule circular DNA that is not derived from multiple-molecule circular DNA, wherein the circular DNA molecule is determined to be single-molecule circular DNA that is not derived from multiple-molecule circular DNA, when two unique sequences contained in the adapter (b) portion are identical to each other, and the circular DNA molecule is determined to be multiple-molecule circular DNA or single-molecule circular DNA derived from the multiple-molecule circular DNA, when the two unique sequences are different from each other.

Furthermore, in a third embodiment, the present invention provides a method for selecting only single-molecule circular DNA that is not derived from multiple-molecule circular DNA in the production of a circular DNA molecule, the method comprising the following steps:

1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the adapter (b) side, such that the adapter (A) in the adapter (B) is located outside of the bond of the DNA molecule to the adapter (b), wherein the adapter (A) comprises a cleavage site generating a cleavage end non-specifically binding to all of the cleavage ends of the adapter (A); and the adapter (b) comprises two unique sequences different depending on each adapter (b), wherein the two unique sequences are identical in sequence and oriented in the same direction or reversely to each other; and between the two unique sequences, the adapter (b) also comprises a cleavage site generating a cleavage end non-specifically binding to all of the cleavage ends of the adapters (b), wherein the cleavage site generates a cleavage end that is not cleaved upon cleaving the cleavage site of the adapter (A) and does not bind to the cleavage end of the adapter (A);

2) a first cleavage step of cleaving the DNA molecule obtained in step 1) at the cleavage site of the adapter (A);

3) a first circularization step of ligating both ends of the DNA molecule obtained in step 2) to circularize the DNA molecule;

4) a step of eliminating an uncircularized linear DNA molecule in step 3);

5) a second cleavage step of cleaving the circular DNA molecule obtained in step 3) and step 4) at the cleavage site of the adapter (b);

6) a second circularization step of ligating both ends of the DNA molecule obtained in step 5) to circularize the DNA molecule; and 7) a step of determining the sequence of the adapter (b) portion of the circular DNA molecule obtained in step 6) and then selecting only single-molecule circular DNA that is not derived from multiple-molecule circular DNA, wherein the circular DNA molecule is determined to be single-molecule circular DNA that is not derived from multiple-molecule circular DNA, when the two unique sequences contained in the adapter (b) portion are identical to each other, and the circular DNA molecule is determined to be multiple-molecule circular DNA or single-molecule circular DNA derived from the multiple-molecule circular DNA, when the two unique sequences are different from each other.

In the first to third embodiments of the present invention, preferably, the adapter (A) is double-stranded DNA comprising a restriction enzyme site generating a cleavage end that is complementary to all of the cleavage ends of the adapter (A), and it is, for example, double-stranded DNA comprising the recognition site of restriction enzyme that recognizes a palindromic sequence ("palindromic restriction enzyme site").

In the first to third embodiments of the present invention, preferably, the adapter (b) comprises two cleavage sites generating a cleavage end non-specifically binding to all of the cleavage ends of the adapter (b). In this case, in a circular DNA molecule for which the second cleavage step has not progressed well, the sequence between the two cleavage sites in the adapter (b) is not eliminated, and thus, such a molecule can be distinguished as an "incomplete clone" by determining the sequence of the adapter (b) and can be eliminated from analysis targets. Such a cleavage site contained in the adapter (b) is preferably a restriction enzyme site, and it is, for example, a palindromic restriction enzyme site.

In the first to third embodiments of the present invention, the number of cleavage sites contained in the adapter (b) is at least one, and preferably two. It may also be a number of 3 or greater. In addition, a pair of identical nick-generating enzyme recognition sites being reversely oriented to each other may be used as cleavage sites contained in the adapter (A) and/or the adapter (b).

In the first to third embodiments of the present invention, preferably, the adapter (A) is a double-stranded DNA complementary to each other comprising a palindromic restriction enzyme site X, and the adapter (B) is a double-stranded DNA complementary to each other having the following structure $Z_1$—Y—$Z_2$-A or $Z_1$—Y—$Z'_2$-A:

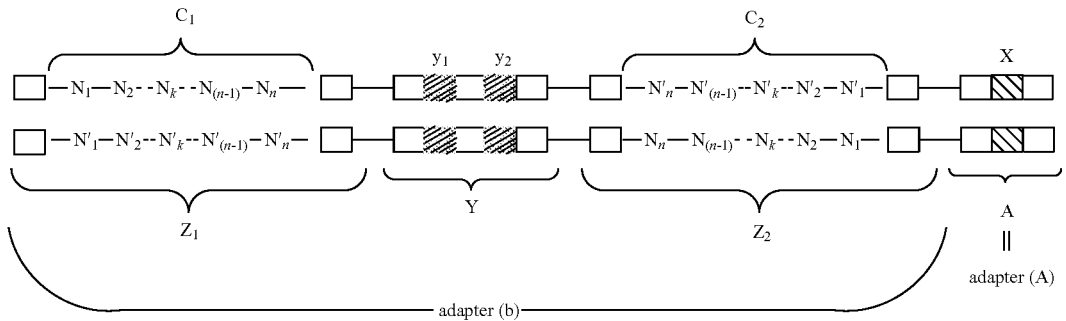

[Formula 1]

wherein
A represents a double-stranded DNA comprising the palindromic restriction enzyme site X, which corresponds to the adapter (A);
$Z_1$—Y—$Z_2$ corresponds to the adapter (b) in the first to third embodiments of the present invention;
Y represents a double-stranded DNA comprising palindromic restriction enzyme sites $y_1$ and $y_2$;
$y_1$ and $y_2$ are identical to each other and generate a cleavage end having a sequence different from X and being not complementary to a cleavage end generated as a result of the cleavage of X;
$Z_1$ and $Z_2$ are double-stranded DNA sequences comprising unique sequences $C_1$ and $C_2$, which are different depending on each adapter, wherein $C_1$ and $C_2$ are identical in sequence and reversely oriented to each other;
n represents an integer of more than 1 and less than 40;
$N_1$ to $N_n$, which may be the same or different, each represent a deoxyribonucleotide selected from the group consisting of dAMP, dCMP, dGMP and dTMP; and
$N'_1$ to $N'_n$ represent the following deoxyribonucleotides respectively corresponding to the $N_1$ to $N_n$.

TABLE 1

| $N_k$ | $N'_k$ |
|---|---|
| dAMP | dTMP |
| dCMP | dGMP |
| dGMP | dCMP |
| dTMP | dAMP | wherein k represents an integer from 1 to n, or wherein
$Z_1$—Y—$Z'_2$ corresponds to the adapter (b) in the first to third embodiments of the present invention;
$Z_1$ and $Z'2$ are double-stranded DNA sequences comprising unique sequences $C_1$ and $C'_2$, which are different depending on each adapter, wherein $C_1$ and $C'_2$ are identical in sequence and oriented in the same direction; and
A, X, Y, $y_1$, $Y_2$, n, $N_1$ to $N_n$, $N'_1$ to $N'_n$, and k have the same definitions as those in the above described structure $Z_1$—Y—$Z_2$-A.

In both of the above structures $Z_1$—Y—$Z_2$-A and $Z_1$—Y—$Z'_2$-A, n is 1 to 40, preferably 4 to 15, and more preferably 5 to 10. However, even when n is more than 40, the method of the present invention can be carried out.

In this embodiment, the palindromic restriction enzyme site X is preferably a BamHI site, an NotI site or a BclI site, and both of the palindromic restriction enzyme sites $y_1$ and $y_2$ are preferably EcoRI sites or PacI sites.

In a fourth embodiment, the present invention provides an adapter for producing a circular DNA consisting of a double-stranded DNA, wherein the two DNA strands are complementary to each other, having the following structure $Z_1$—Y—$Z_2$-A or $Z_1$—Y—$Z''_2$-A, wherein the adapter enables to select only single-molecule circular DNA that is not derived from multiple-molecule circular DNA from a group of the circular DNA molecules produced using the adapter:

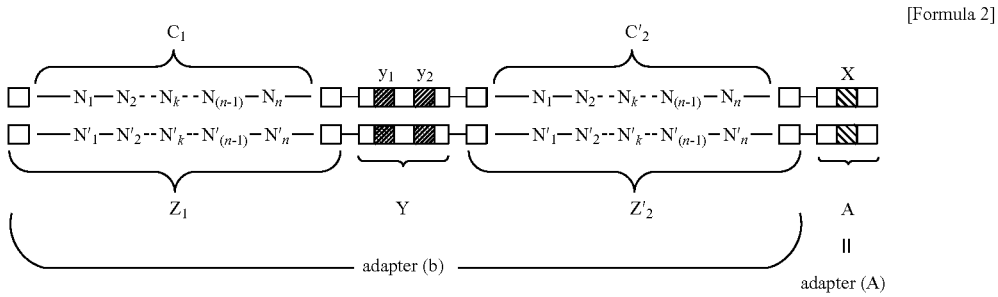

[Formula 2]

[Formula 3]

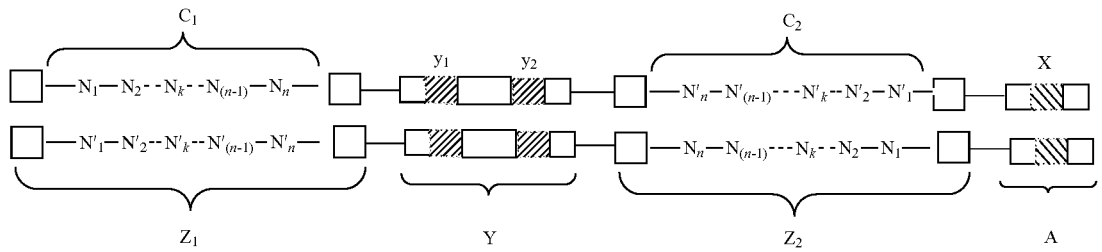

wherein
A represents a double-stranded DNA comprising the palindromic restriction enzyme site X;
Y represents a double-stranded DNA comprising palindromic restriction enzyme sites $y_1$ and $y_2$;
$y_1$ and $y_2$ are identical to each other and generate a cleavage end having a sequence different from X and being not complementary to a cleavage end generated as a result of the cleavage of X;
$Z_1$ and $Z_2$ are double-stranded DNA sequences comprising unique sequences $C_1$ and $C_2$, which are different depending on each adapter, wherein $C_1$ and $C_2$ are identical in sequence and reversely oriented to each other;
n represents an integer of more than 1 and less than 40;
$N_1$ to $N_n$, which may be the same or different, each represent a deoxyribonucleotide selected from the group consisting of dAMP, dCMP, dGMP and dTMP; and
$N'_1$ to $N'_n$ represent the following deoxyribonucleotides respectively corresponding to the $N_1$ to $N_n$,

TABLE 2

| $N_k$ | $N'_k$ |
|---|---|
| dAMP | dTMP |
| dCMP | dGMP |
| dGMP | dCMP |
| dTMP | dAMP | wherein k represents an integer from 1 to n, or

In both of the above structures $Z_1$—Y—$Z_2$-A and $Z_1$—Y—$Z'_2$-A, n is 1 to 40, preferably 4 to 15, and more preferably 5 to 10. However, even when n is more than 40, the method of the present invention can be carried out.

The above described adapter in the fourth embodiment of the present invention corresponds to the adapter (B) in the first to third embodiments of the present invention. This adapter is preferably used in the method of the present invention for producing a group of circular DNA molecules, the method of the present invention for producing a single-molecule circular DNA that is not derived from multiple-molecule circular DNA, and the method of the present invention for selecting only single-molecule circular DNA that is not derived from multiple-molecule circular DNA.

In the fourth embodiment of the present invention, the palindromic restriction enzyme site X is preferably a BamHI site, an NotI site or a BclI site, and both of the palindromic restriction enzyme sites $y_1$ and $y_2$ are preferably EcoRI sites or PacI sites.

In a fifth embodiment, the present invention further provides a kit for producing a circular DNA comprising the adapter according to the above described fourth embodiment (which is also simply referred to as adapter (B)) and an adapter consisting of a double-stranded DNA comprising a restriction enzyme site identical to the restriction enzyme site X comprised in the adapter (B) (which is also simply referred to as adapter (A)), wherein the kit enables to select only single-molecule circular DNA that is not derived from mul-

[Formula 4]

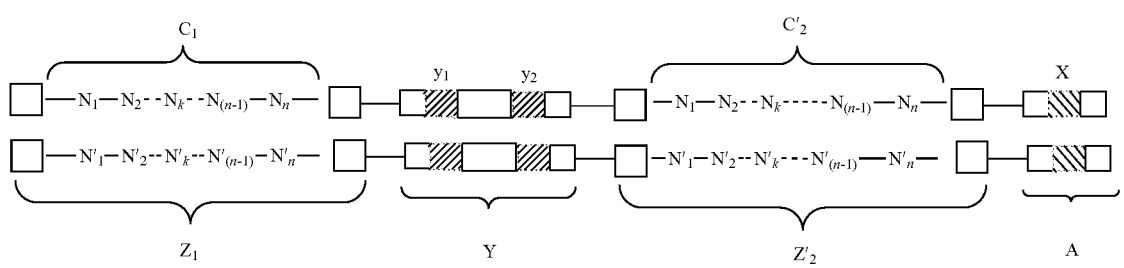

wherein
$Z_1$ and $Z'_2$ are double-stranded DNA sequences comprising unique sequences $C_1$ and $C'_2$, which are different depending on each adapter, wherein $C_1$ and $C'_2$ are identical in sequence and oriented in the same direction; and
A, X, Y, $y_1$, $y_2$, n, $N_1$ to $N_n$, $N'_1$ to $N'_n$, and k have the same definitions as those in the above described structure $Z_1$—Y—$Z_2$-A.

tiple-molecule circular DNA from a group of circular DNA molecules produced using the kit.

In a sixth embodiment, the present invention further provides: a method for producing a cDNA library using the method in the above described first embodiment, wherein the library is capable of selecting only single-molecule circular DNA that is not derived from multiple-molecule circular DNA from the library; and a method for producing a cDNA library consisting only of single-molecule circular DNA that is not derived from multiple-molecule circular DNA, using the method in the above described second or third embodiment.

In a seventh embodiment, the present invention further provides a method for identifying a gene by subjecting a circular DNA molecule to a mate-pair method, the method comprising the following steps:
1) a step of reading nucleotide sequences each consisting of 15 nucleotides or more and 600 nucleotides or less that are flanking to both sides of an adapter (B), in the group of circular DNA molecules produced by the method in the first embodiment of the present invention, the single-molecule circular DNA that is not derived from multiple-molecule circular DNA produced by the method in the second embodiment of the present invention, or the single-molecule circular DNA that is not derived from multiple-molecule circular DNA, which is selected by the method in the third embodiment of the present invention, wherein when the group of circular DNA molecules produced by the method in the first embodiment of the present invention is used, the method further comprises a step of selecting only the single-molecule circular DNA that is not derived from multiple-molecule circular DNA by determining the sequence of the adapter (b) portion, before the step, or at the same time as the step, or after the step; and
2) a step of identifying a gene contained in the single-molecule circular DNA that is not derived from multiple-molecule circular DNA by comparing the nucleotide sequences read in step 1) with the sequences of both ends of a known gene.

The nucleotide sequence to be read consists of preferably 15 to 100 nucleotides, and more preferably 25 to 35 nucleotides. However, the method of the present invention can also be carried out by reading a nucleotide sequence consisting of 600 or more nucleotides.

In an eighth embodiment, the present invention further provides a method for detecting a fusion gene by subjecting a circular DNA molecule to a mate-pair method, the method comprising the following steps:
1) a step of reading nucleotide sequences each consisting of 15 nucleotides or more and 600 nucleotides or less that are flanking to both sides of an adapter (B), in the group of circular DNA molecules produced by the method in the first embodiment of the present invention, the single-molecule circular DNA that is not derived from multiple-molecule circular DNA produced by the method in the second embodiment of the present invention, or the single-molecule circular DNA that is not derived from multiple-molecule circular DNA, which is selected by the method in the third embodiment of the present invention, wherein when the group of circular DNA molecules produced by the method in the first embodiment of the present invention is used, the method further comprises a step of selecting only the single-molecule circular DNA that is not derived from multiple-molecule circular DNA by determining the sequence of the adapter (b) portion, before the step, or at the same time as the step, or after the step; and
2) a step of comparing the nucleotide sequences read in step 1) with the sequences of both ends of a known gene, wherein when the genes of both ends correspond to known different genes, the gene comprised in the single-molecule circular DNA that is not derived from multiple-molecule circular DNA is identified to be a fusion gene.

The nucleotide sequence to be read consists of preferably 15 to 100 nucleotides, and more preferably 25 to 35 nucleotides. However, the method of the present invention can also be carried out by reading a nucleotide sequence consisting of 600 or more nucleotides.

In the eighth embodiment of the present invention, when the sequences of both sides flanking to both sides of the adapter (B) correspond to the ends of both sides of a known fusion gene, the known fusion gene is detected. When the relationship between the known fusion gene and a disease has been known, there is provided a method for detecting a disease characterized by the expression of the fusion gene detected by the method of the eighth embodiment, wherein the fusion gene is used as a marker.

On the other hand, when the sequences flanking to both sides of the adapter (B) correspond to the terminal sequences of different genes and do not correspond to the ends of both sides of a known fusion gene, the gene contained in the circular DNA molecule or the single-molecule circular DNA is identified to be a novel fusion gene. In this case, the detected novel fusion gene is preferably used in drug discovery screening.

Effects of Invention

Using the adapter and method of the present invention, the accuracy of gene analysis is dramatically improved. Specifically, using the adapters and methods of the present invention, single-molecule circular DNA that is not derived from multiple-molecule circular DNA can be completely distinguished from multiple-molecule circular DNA and also from single-molecule circular DNA derived from the multiple-molecule circular DNA. As a result, only the single-molecule circular DNA that is not derived from multiple-molecule circular DNA can be selected at a probability of almost 100%. As a result, unconventional high-accuracy mate-pair analysis becomes possible, and thus, the adapter and method of the present invention are provided as tools extremely useful for genomic analysis. In particular, by applying the method of the present invention to the production of a cDNA library, it is highly likely to discover a novel fusion gene. That is to say, multiple-molecule circular DNA, which causes a problem in mate-pair analysis, is eliminated at the stage of sequence analysis, and only single-molecule circular DNA that is not derived from multiple-molecule circular DNA is selected, so that a novel diagnostic tool and/or method can be developed.

According to the present invention, there is provided a method for selecting only single-molecule circular DNA that is not derived from multiple-molecule circular DNA upon circularization of DNA. Accordingly, problems regarding contamination in gene analysis such as mate-pair analysis can be solved, and so that high-accuracy analysis becomes possible. Moreover, by applying the method of the present invention to detection and/or analysis of a fusion gene, high-accuracy analysis of a fusion gene becomes possible, and a useful diagnostic tool can be provided.

BRIEF DESCRIPTION OF DRAWINGS

FIG. 9 is a schematic view showing application of the method of the present invention to cDNA synthesized from mRNA.

DESCRIPTION OF EMBODIMENTS

Figure 1:
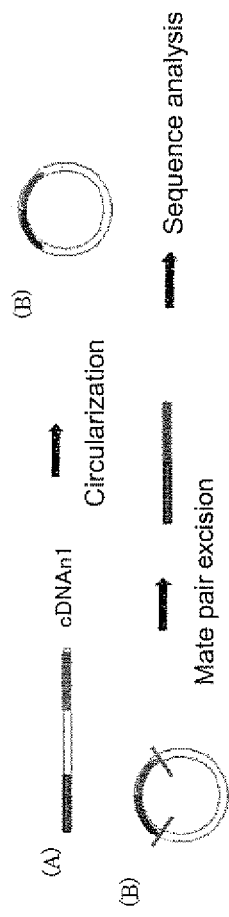
FIG. 1 schematically shows an outline of the gene analysis according to the mate-pair method.
Figure 2:
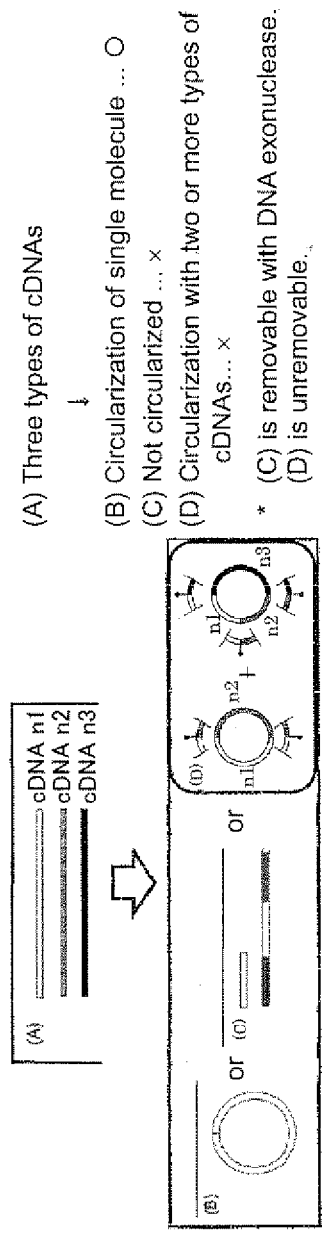
FIG. 2 schematically shows problems with the gene analysis according to the mate-pair method.
Figure 3:
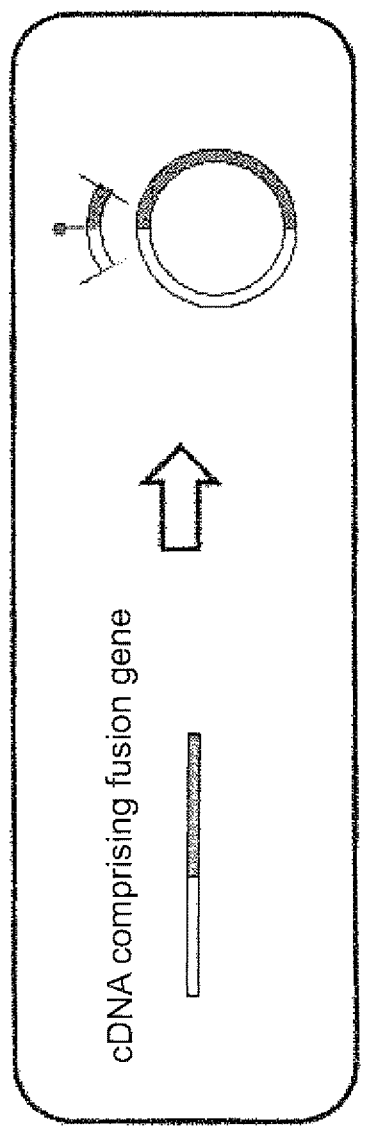
FIG. 3 is a schematic view showing the analysis of a fusion gene according to the mate-pair method.
Figure 4:
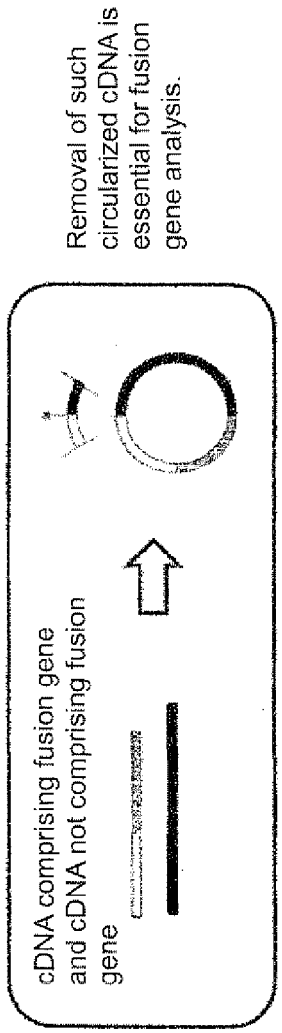
FIG. 4 schematically shows problems with the analysis of a fusion gene according to the mate-pair method.

A First Embodiment of the Present Invention

In a first embodiment, the present invention provides a method for producing a group of circular DNA molecules, the method comprising the following steps, wherein the method enables to select only single-molecule circular DNA that is not derived from multiple-molecule circular DNA from a group of circular DNA molecules produced by the method:
1) a step of binding an adapter (A) for a first circularization to one end of each DNA molecule of interest, and binding to the other end thereof an adapter (B) used for a second circularization comprising an adapter (b) and the adapter (A), wherein the adapter (B) binds to the DNA molecule via the adapter (b) side, such that the adapter (A) in the adapter (B) is located outside of the bond of the DNA molecule to the adapter (b), wherein
 the adapter (A) comprises a cleavage site generating a cleavage end non-specifically binding to all of the cleavage ends of the adapter (A), and
 the adapter (b) comprises two unique sequences different depending on each adapter (b), wherein the two unique sequences are identical in sequence and oriented in the same direction or reversely to each other; and
 between the two unique sequences, the adapter (b) also comprises a cleavage site generating a cleavage end non-specifically binding to all of the cleavage ends of the adapters (b), wherein the cleavage site generates a cleavage end that is not cleaved upon cleaving the cleavage site of the adapter (A) and does not bind to the cleavage end of the adapter (A);
2) a first cleavage step of cleaving the DNA molecule obtained in step 1) at the cleavage site of the adapter (A);
3) a first circularization step of binding both ends of the DNA molecule obtained in step 2) to circularization the DNA molecule;
4) a step of eliminating an uncircularized linear DNA molecule in step 3);
5) a second cleavage step of cleaving the circular DNA molecule obtained in step 3) and step 4) at the cleavage site of the adapter (b); and
6) a second circularization step of binding both ends of the DNA molecule obtained in step 5) to circularization the DNA molecule;
 wherein the circular DNA molecule obtained in step 6) is determined to be single-molecule circular DNA that is not derived from multiple-molecule circular DNA, when two unique sequences contained in an adapter (b) portion are identical to each other as a result of determination of the sequence of the adapter (b) portion, and the circular DNA molecule obtained in step 6) is determined to be multiple-molecule circular DNA or single-molecule circular DNA derived from the multiple-molecule circular DNA, when the two unique sequences are different from each other.

The above described first embodiment of the present invention is a technique capable of producing a circular DNA molecule having a specific structure that enables to distinguish single-molecule circular DNA that is not derived from multiple-molecule circular DNA from multiple-molecule circular DNA and also from single-molecule circular DNA derived from the multiple-molecule circular DNA. Specifically, the method of the first embodiment of the present invention is characterized in that it comprises two-step circularization.

Hereinafter, the method of the first embodiment according to the present invention will be described in the order of steps.

Step 1) is a step of binding an adapter (A) for a first circularization to one end of each DNA molecule of interest, and binding to the other end thereof an adapter (B) used for a second circularization comprising an adapter (b) and the adapter (A). Herein, the adapter (B) binds to the DNA molecule via the adapter (b) side, such that the adapter (A) in the adapter (B) is located outside of the bond of the DNA molecule to the adapter (b). Specifically, the adapter (A) is allowed to bind to one end of each DNA molecule of interest, and the adapter (B) is allowed to bind to the other end, so that the adapter (A) in the adapter (B) is located on the side closer to the end than the adapter (b) is. As a result, the adapters (A) are located on both ends of each DNA molecule of interest.

It is to be noted that the adapter (A) comprises a cleavage site generating a cleavage end non-specifically binding to all of the cleavage ends of the adapter (A). That is to say, the adapter (A) does not exhibit binding specificity and enables non-specific binding between all cleavage ends from the adapter (A). On the other hand, the adapter (b) comprises two unique sequences that are different depending on each adapter (b), and the two unique sequences are identical in sequence and oriented in the same direction or are reversely oriented to each other. In addition, the adapter (b) comprises a cleavage site generating a cleavage end non-specifically binding to all of the cleavage ends of the adapter (b) between the two unique sequences, and the cleavage site generates a cleavage end that is not cleaved when the cleavage site of the adapter (A) is cleaved and is not complementary to the cleavage end of the adapter (A). That is, the adapter (b) does not show binding specificity, and cleavage ends derived from all adapters (b) can be non-selectively bound to one another. The same applies in a case in which the number of cleavage sites contained in the adapter (b) is 1, 2, 3 or more.

Step 2) is a first cleavage step of cleaving the DNA molecule obtained in step 1) at the cleavage site of the adapter (A). Since the adapters (A) bind to both ends of the DNA molecule obtained in step 1), cleavage ends from the adapters (A) are generated on both ends of each DNA molecule as a result of the first cleavage step.

Step 3) is a first circularization step of binding bath ends of the DNA molecule obtained in step 2) to circularize the DNA molecule. The first circularization is circularization with the adapters (A), and such circularization occurs as a result that cleavage ends from the adapters (A) generated on both ends of each DNA molecule bind to each other. Herein, the adapter (B), as well as the adapters (A), is incorporated into the circular molecule during the first circularization. As described above, the function of the adapter (A) does not have specificity, and does not have selectivity regarding the rebinding of both ends of the DNA molecule of interest. Thus, not only the binding of both ends of a single DNA molecule at the adapter (A) portions, but circularization by the binding of both ends of each of a plurality of DNA molecules, also takes place. That is, because of the function of the adapter (A), circularization of a plurality of molecules, as well as single-molecule circularization, takes place. A circularized product from such a plurality of molecules naturally comprises a plurality of the adapters (B).

Step 4) is a step of eliminating an uncircularized linear DNA molecule in step 3). The linear DNA molecules can be eliminated, for example, by allowing exonuclease to act on them.

Step 5) is a second cleavage step of cleaving the circular DNA molecule obtained in step 3) and step 4) at the cleavage site of the adapter (b). That is to say, cleavage is carried out at the adapter (b) incorporated into each DNA molecule that has been circularized in step 3), such that a linear molecule is generated. By the second cleavage step, cleavage ends from the adapters (b) are generated on both ends of each DNA molecule. In this step, the cleavage end generated as a result of the cleavage non-specifically binds to all of the cleavage ends of the adapter (b).

Step 6) is a second circularization step of binding both ends of the DNA molecule obtained in step 5) to circularize the DNA molecule. That is to say, the cleavage ends from the adapters (b) are present on both ends of each DNA molecule obtained in step 5). As a result of the binding of cleavage ends derived from the adapters (b), second circularization takes place. Uncircularized linear molecules can be separated and eliminated by allowing exonuclease to act on them.

In the second circularization step, other than circularization with a single DNA molecule, circularization with multiple DNA molecules may take place. However, the probability of the rebinding and circularization in a plurality of the original molecules that have been bound before the second cleavage step is extremely low and is substantially 0 (zero), as described later.

Accordingly, the following five types of molecules may be generated as a result of the second circularization step:
(1) "single-molecule circular DNA that is not derived from multiple-molecule circular DNA" (for example, A4 of FIG. 6), wherein the single-molecule circular DNA is formed by self-circularization of single-molecule DNA (for example, A3 of FIG. 6) that is generated by cleaving by the second cleavage step, the single-molecule circular DNA (for example, A2 of FIG. 6) formed by the first circularization step;
(2) "single-molecule circular DNA derived from multiple-molecule circular DNA" (for example, B4-1 of FIG. 6), wherein the single-molecule circular DNA is formed by self-circularization of single-molecule DNA (for example, 83 of FIG. 6) that is generated by cleaving by the second cleavage step, the multiple-molecule circular DNA (for example, 82 of FIG. 6) formed by the first circularization step;
(3) "multiple-molecule circular DNA-1" (for example, B4-2 of FIG. 6), wherein the DNA-1 is formed by the binding and circularization of a plurality of single-molecule DNAs (for example, B3 of FIG. 6) generated by cleaving by the second cleavage step, the multiple-molecule circular DNA (for example, B2 of FIG. 6) formed by the first circularization step;
(4) "multiple-molecule circular DNA-2" (for example, B4-3 of FIG. 6), wherein the DNA-2 is formed by the binding and circularization of single-molecule DNA (for example, A3 of FIG. 6) generated by cleaving by the second cleavage step, the single-molecule circular DNA (for example, A2 of FIG. 6) formed by the first circularization step, and single-molecule DNA (for example, B3 of FIG. 6) generated by cleaving by the second cleavage step, the multiple-molecule circular DNA (for example, B2 of FIG. 6) formed by the first circularization step; and
(5) "multiple-molecule circular DNA-3" (for example, B4-4 of FIG. 6), wherein the DNA-3 is formed by the binding and circularization of a plurality of single-molecule DNAs (for example, A3 of FIG. 6) generated by cleaving by the second cleavage step, the single-molecule circular DNA (for example, A2 of FIG. 6) formed by the first circularization step.

Herein, when circularization has occurred with multiple unpaired molecules which had been bound to one another before the second cleavage step (the aforementioned (3), (4) or (5)), two different unique sequences are present in parallel in the adapter (b) portion. Thus, by determining the sequence of the adapter (b) portion, such multiple-molecule circular DNA can be eliminated as an undesired clone (see B4-2, B4-3 and B4-4 of FIG. 6, and FIG. 7).

Figure 6:
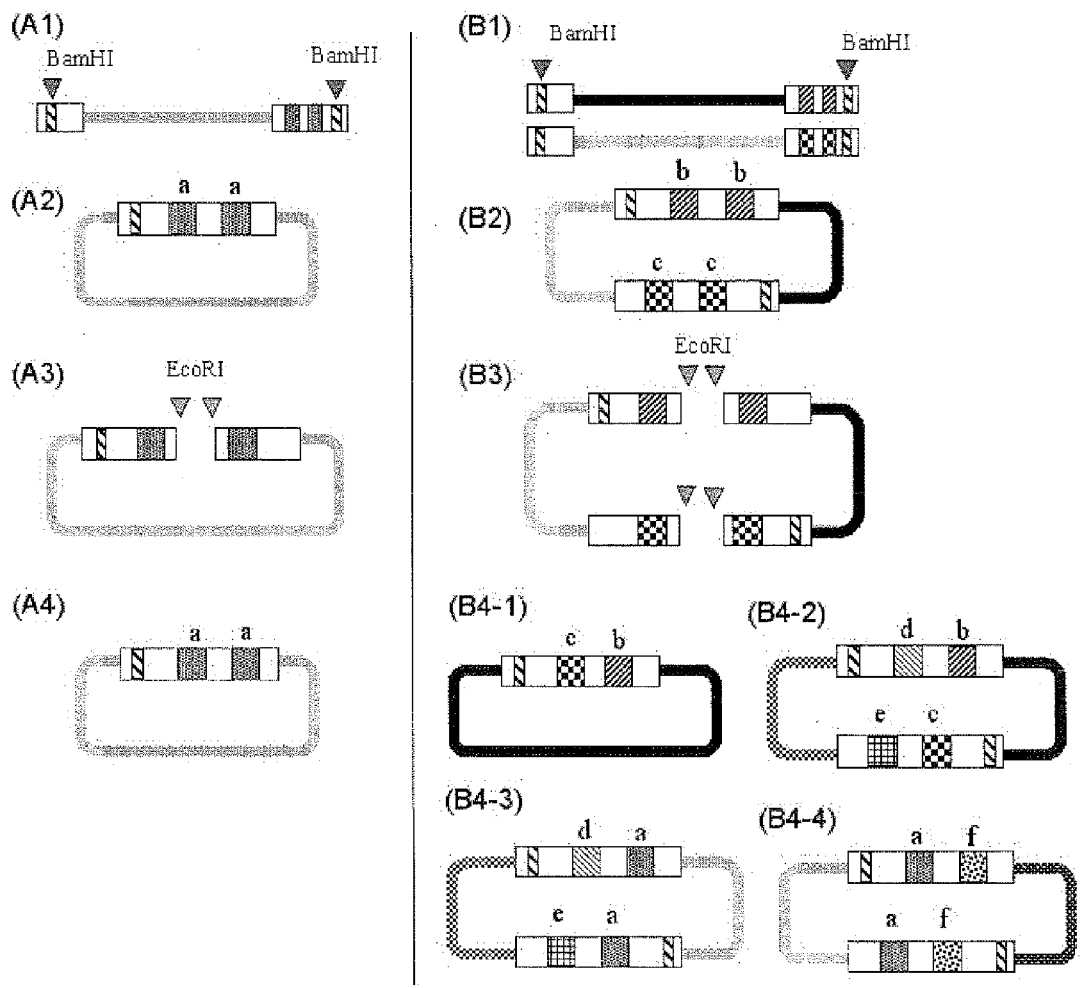
FIG. 6 schematically shows first cleavage, first circularization, second cleavage, and second circularization steps in the method for producing a circular DNA molecule according to the present invention. For convenience, different unique sequences are distinguished from one another using the symbols a, b, c, d, e and f.
Figure 7:
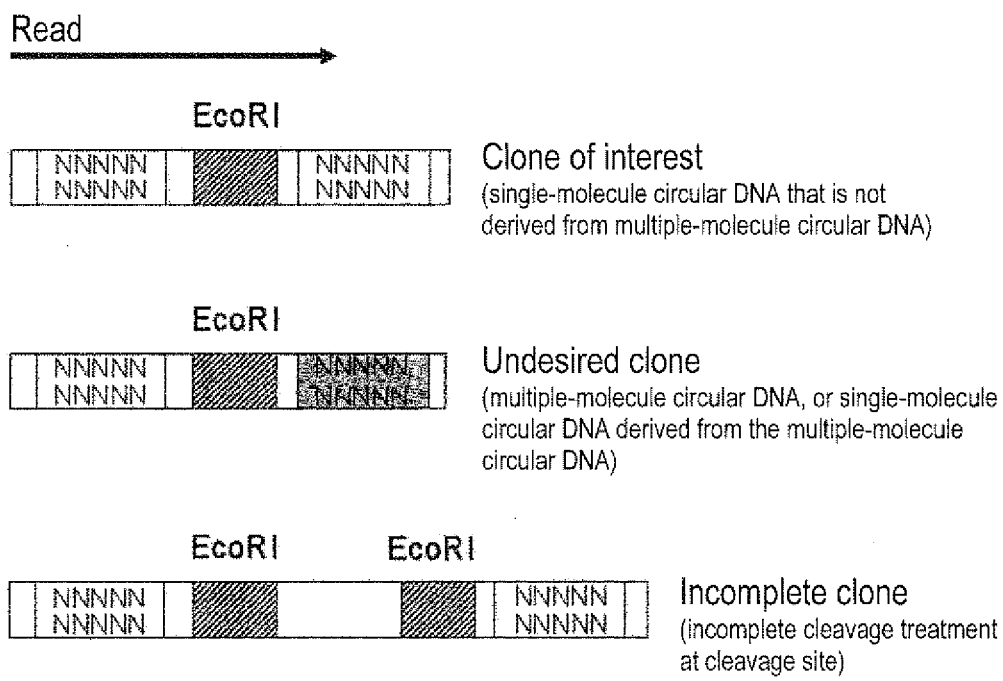
FIG. 7 schematically shows a structure of an adapter (b) portion that can be generated after the second circularization step. In the figure, NNNNN indicates a unique sequence. By determining the sequence of such a region, a clone of interest, an undesired clone, and an incomplete clone can be distinguished from one another.

Moreover, in the case of the single-molecule circular DNA derived from multiple-molecule circular DNA (the aforementioned (2)), since two different unique sequences are present in parallel in the adapter (b) portion, even when the sequence of the adapter (b) portion is determined, it cannot be distinguished from the multiple-molecule circular DNA (B4-1 of FIG. 6, and FIG. 7). Hence, in the method of the present invention, such single-molecule circular DNA becomes also a target to be eliminated as an undesired clone.

Accordingly, it is only the single-molecule circular DNA that is not derived from multiple-molecule circular DNA (the aforementioned (1)), in which two identical unique sequences are present in the adapter (b) after the second circularization step (A4 of FIG. 6).

When different molecules each having the same adapter (b) bind to each other to form multiple-molecule circular DNA in the first circularization step, single-molecule circular DNA, in which two identical unique sequences are present in parallel, may be generated through the second cleavage step and the second circularization step. However, the probability of generating such single-molecule circular DNA can bring as close as possible to 0 (zero) by extending the length of the unique sequence (namely, increasing the type of adapters (b)), as described later. When the unique sequence has a certain length, the probability becomes substantially 0 (zero). Thus, it does not cause problem.

As given above, when two unique sequences contained in an adapter (b) portion are identical to each other by determining the sequence of the adapter (b) portion, the circular DNA molecule obtained in step 6) can be determined to be single-molecule circular DNA that is not derived from multiple-molecule circular DNA. When the two unique sequences are different from each other, the circular DNA molecule obtained in step 6) can be determined to be multiple-molecule circular DNA or single-molecule circular DNA derived from the multiple-molecule circular DNA.

As far as the adapters (A) and (b) perform the above-mentioned functions, the structures thereof are not particularly limited. For example, when these adapters are double-stranded DNAs, an example of the adapter (A) is an adapter comprising a palindromic restriction enzyme site, and an example of the adapter (b) is an adapter comprising two identical unique sequences that are reversely oriented to each other and also comprising two palindromic restriction enzyme sites between the two unique sequences. However, the adapters (A) and (b) are not limited thereto. For example, the adapter (b) may comprise two identical unique sequences and may also comprise only one or three or more of cleavage sites that generate a cleavage end non-specifically binding to all of the cleavage ends of the adapter (b) between the two unique sequences. In short, circular DNA is cleaved at cleavage sites between unique sequences and then the generated cleavage ends are rebound to each other, so that a structure may be formed, in which two identical or different unique sequences are aligned, depending on the origin of the circular DNA (namely, it is single-molecule circular DNA that is not derived from multiple-molecule circular DNA, or multiple-molecule circular DNA, or single-molecule circular DNA derived from the multiple-molecule circular DNA).

A non-palindromic restriction enzyme site can also be used as a cleavage site, as long as it generates cleavage ends complementary to each other. In addition, it is also possible to use a pair of identical nick-generating enzyme recognition sites that are reversely oriented to each other, instead of restriction enzyme sites. For example, when a BbsI recognition site that is a non-palindromic restriction enzyme is used, since cleavage ends are generated outside of the recognition site, cleavage ends complementary to each other can be generated by designing the sequence, e.g. applying a palindromic structure to a sequence as a cleavage end portion.

As a restriction enzyme site, the recognition site of a restriction enzyme (what is called "rare cutter"), which recognizes a rare gene sequence that hardly cleaves DNA of interest, is preferable. An example of a palindromic restriction enzyme site as a rare cutter, which recognizes 8 nucleotides, is the following PacI site.

[Formula 5]
PacI
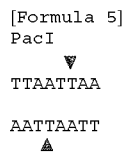
TTAATTAA

AATTAATT
▲

After completion of restriction enzyme cleavage, a cohesive end that is designed to be a non-palindrome (non-palindromic structure) is anticipated to increase the efficiency of circularization with single-molecule DNA, and for example, it is also possible to introduce a restriction enzyme site, such as the following SfiI site.

[Formula 6]
SfiI
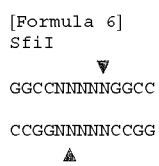
GGCCNNNNNGGCC

CCGGNNNNNCCGG
▲

Herein, NNNNN is determined as follows in an upstream and a downstream, for example.

[Formula 7]
AAATT

TTTAA

Likewise, it is also possible to introduce a Type II restriction enzyme recognition site, such as the following BbsI site.

[Formula 8]
BbsI
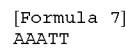
GAAGACNNNNNN

CTTCTGNNNNNN
▲

On the other hand, even in the case of using an EcoRI site, only the restriction enzyme site in the adapter is cleaved by previously treating cDNA with EcoRI methylase, so that cDNA can be prevented from being cleaved.

For the similar purpose as described above, by introducing methylated bases into an adapter, only the restriction enzyme site in the adapter can be cleaved, such as the following SgeI restriction enzyme site.

[Formula 9]
SgeI
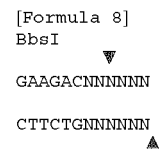
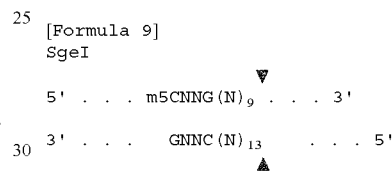

SgeI cleaves the target DNA containing 5-methyl cyctosine (m5c) on either or both of the chains.

Moreover, when a non-palindromic restriction enzyme site is used as an adapter (A), sequences are designed or selected, such that a single adapter (A) (which is referred to as "A1") is distinguished from an adapter (A) contained in an adapter (B) (which is referred to as "A2"), the adapters "A1" and "A2" bind to each other, but two "A1" or two "A2" do not bind to each other. In this case, it is expected that the efficiency of forming single-molecule circular DNA at a first stage will be slightly increased in comparison with an ordinary adapter (A).

According to the first embodiment of the present invention, it becomes possible to determine whether the produced circular DNA is single-molecule circular DNA that is not derived from multiple-molecule circular DNA, or multiple-molecule circular DNA, or single-molecule circular DNA derived from the multiple-molecule circular DNA (which would become a contaminant in analysis), for example, in gene analysis or gene identification according to the mate-pair method.

A Second Embodiment of the Present Invention

In a second embodiment, the present invention provides a method for producing a single-molecule circular DNA that is not derived from multiple-molecule circular DNA, the method comprising the following steps:
1) a step of producing a circular DNA molecules by the method according to the first embodiment of the present invention; and
2) a step of determining the sequence of an adapter (b) portion in the produced circular DNA molecules and selecting only single-molecule circular DNA that is not derived from multiple-molecule circular DNA, wherein the circular DNA molecule is determined to be single-molecule circular DNA that is not derived from multiple-molecule circular DNA, when two unique sequences contained in the adapter (b) portion are identical to each other, and the circular DNA molecule is determined to be multiple-molecule circular DNA or single-molecule circular DNA derived from the multiple-molecule circular DNA, when the two unique sequences are different from each other.

The circular DNA molecule produced by the method of the first embodiment of the present invention is any of single-molecule circular DNA that is not derived from multiple-molecule circular DNA, multiple-molecule circular DNA, and single-molecule circular DNA derived from the multiple-molecule circular DNA. The second embodiment of the present invention is a method for determining the sequence of an adapter (b) portion in a group of circular DNA molecules consisting of these circular DNAs, so as to obtain only single-molecule circular DNA that is not derived from multiple-molecule circular DNA from the aforementioned group.

A Third Embodiment of the Present Invention

In a third embodiment, the present invention provides a method for selecting only single-molecule circular DNA that is not derived from multiple-molecule circular DNA in the production of circular DNA molecules, the method comprising the following steps:

1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the adapter (b) side, such that the adapter (A) in the adapter (B) is located outside of the bond of the DNA molecule to the adapter (b), wherein the adapter (A) comprises a cleavage site generating a cleavage end non-specifically binding to all of the cleavage ends of the adapter (A); and the adapter (b) comprises two unique sequences different depending on each adapter (b), wherein the two unique sequences are identical in sequence and oriented in the same direction or reversely to each other; and between the two unique sequences, the adapter (b) also comprises a cleavage site generating a cleavage end non-specifically binding to all of the cleavage ends of the adapters (b), wherein the cleavage site generates a cleavage end that is not cleaved upon cleaving the cleavage site of the adapter (A) and does not bind to the cleavage end of the adapter (A);

2) a first cleavage step of cleaving the DNA molecule obtained in step 1) at the cleavage site of the adapter (A);

3) a first circularization step of binding both ends of the DNA molecule obtained in step 2) to circularize the DNA molecule;

4) a step of eliminating an uncircularized linear DNA molecule in step 3);

5) a second cleavage step of cleaving the circular DNA molecule obtained in step 3) and step 4) at the cleavage site of the adapter (b);

6) a second circularization step of binding both ends of the DNA molecule obtained in step 5) to circularize the DNA molecule; and 7) a step of determining the sequence of the adapter (b) portion of the circular DNA molecule obtained in step 6) and then selecting only single-molecule circular DNA that is not derived from multiple-molecule circular DNA, wherein the circular DNA molecule is determined to be single-molecule circular DNA that is not derived from multiple-molecule circular DNA, when the two unique sequences contained in the adapter (b) portion are identical to each other, and the circular DNA molecule is determined to be multiple-molecule circular DNA or single-molecule circular DNA derived from the multiple-molecule circular DNA, when the two unique sequences are different from each other.

Step 1) to step 6) in the third embodiment of the present invention are identical to step 1) to step 6) in the first embodiment of the present invention.

Step 7) in the third embodiment of the present invention is a step of determining the sequences of the adapter (b) portions of the circular DNA molecules obtained in step 6) and then selecting only single-molecule circular DNA that is not derived from multiple-molecule circular DNA. As described above regarding the first embodiment of the present invention, the circular DNA molecule obtained in step 6), in which two unique sequences in the adapter (b) are identical to each other, is only single-molecule circular DNA that is not derived from multiple-molecule circular DNA. Accordingly, by determining the sequence in the adapter (b) so as to determine whether the two unique sequences are identical to or different from each other, the circular DNA molecule obtained in step 6) can be determined to be single-molecule circular DNA that is not derived from multiple-molecule circular DNA, or multiple-molecule circular DNA, or single-molecule circular DNA derived from the multiple-molecule circular DNA, and only the single-molecule circular DNA that is not derived from multiple-molecule circular DNA can be selected as an analysis target.

According to the third embodiment of the present invention, it becomes possible to eliminate from analysis targets, multiple-molecule circular DNA and single-molecule circular DNA derived from the multiple-molecule circular DNA, which become a contaminants, for example, in gene analysis or gene identification according to the mate-pair method, and to select only the single-molecule circular DNA that is not derived from multiple-molecule circular DNA as an analysis target.

In the first to third embodiments of the present invention, preferably, the adapter (A) is a double-stranded DNA complementary to each other comprising a palindromic restriction enzyme site X, and the adapter (B) is a double-stranded DNA complementary to each other having the following structure $Z_1$—Y—$Z_2$-A or $Z_1$—Y—$Z'_2$-A:

[Formula 10]

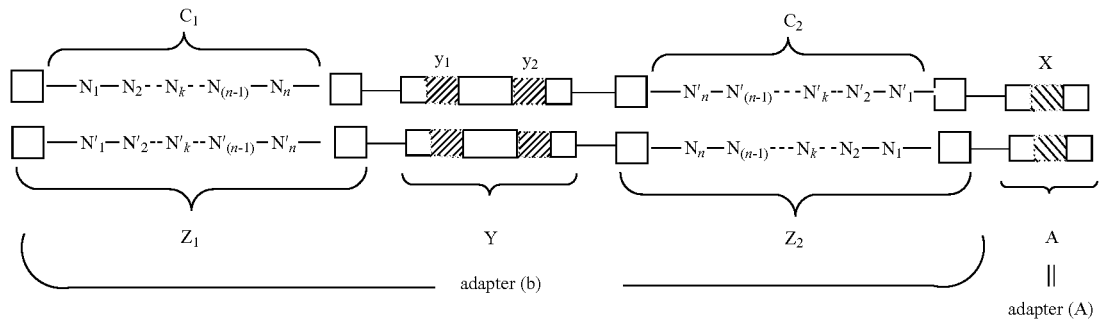

wherein
A represents a double-stranded DNA comprising the palindromic restriction enzyme site X, which corresponds to the adapter (A);
$Z_1$—Y—$Z_2$ corresponds to the adapter (b) in the first to third embodiments of the present invention;
Y represents a double-stranded DNA comprising palindromic restriction enzyme sites $y_1$ and $y_2$;
$y_1$ and $y_2$ are identical to each other and generate a cleavage end having a sequence different from X and being not complementary to a cleavage end generated as a result of the cleavage of X;
$Z_1$ and $Z_2$ are double-stranded DNA sequences comprising unique sequences $C_1$ and $C_2$, which are different depending on each adapter, wherein $C_1$ and $C_2$ are identical in sequence and reversely oriented to each other;
n represents an integer of more than 1 and less than 40;
$N_2$ to $N_n$, which may be the same or different, each represent a deoxyribonucleotide selected from the group consisting of dAMP, dCMP, dGMP and dTMP; and
$N'_1$ to $N'_n$ represent the following deoxyribonucleotides respectively corresponding to the $N_2$ to $N_n$,

TABLE 3

| $N_k$ | $N'_k$ |
|---|---|
| dAMP | dTMP |
| dCMP | dGMP |
| dGMP | dCMP |
| dTMP | dAMP | wherein k represents an integer from 1 to n, or $Z_1$ and $Z'_2$ are double-stranded DNA sequences comprising unique sequences $C_1$ and $C'_2$, which are different depending on each adapter, wherein $C_1$ and $C'_2$ are identical in sequence and oriented in the same direction; and
A, X, Y, $y_1$, $y_2$, n, $N_1$ to $N_n$, $N'_1$ to $N'_n$, and k have the same definitions as those in the above described structure $Z_1$—Y—$Z_2$-A.

In both of the above structures $Z_1$—Y—$Z_2$-A and $Z_1$—Y—$Z'_2$-A, n is 1 to 40, preferably 4 to 15, and more preferably 5 to 10. However, even when n is more than 40, the method of the present invention can be carried out.

Such a preferred adapter (A) is a sequence that is used in cleavage with restriction enzymes in the first cleavage step and is then used in ligation of cleavage ends for the purpose of obtaining circular DNA. Accordingly, the adapter (A) may comprise any restriction enzyme site, as long as the restriction enzyme site is a palindromic restriction enzyme site. The adapter (A) preferably comprises a restriction enzyme site that recognizes a rare gene sequence that hardly cleaves DNA of interest. Examples of the restriction enzyme site X contained in the adapter (A) include the following BamHI site, NotI site, and BclI site.

[Formula 12]
```
BamHI        NotI         BclI
  ▼           ▼            ▼
GGATCC       GCGGCCGC     TGATCA

CCTAGG       CGCCGGCG     ACTAGT
     ▲            ▲            ▲
```

[Formula 11]

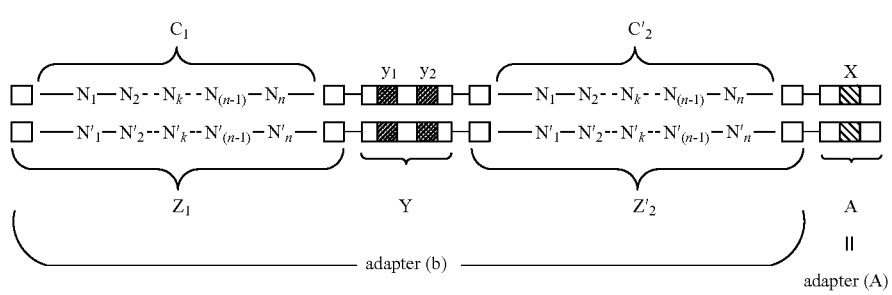

wherein
$Z_1$—Y—$Z'_2$ corresponds to the adapter (b) in the first to third embodiments of the present invention;

Preferred examples of the sequence of the adapter (A) are shown in SEQ ID NO: 1 (forward direction chain) and SEQ ID NO: 2 (reverse direction chain).

Such a preferred adapter (B) is a sequence that is used in cleavage with restriction enzymes in the second cleavage step and is then used in ligation of cleavage ends in an expectation of recircularization of the cleaved DNA molecules. Accordingly, the adapter (B) may comprise any restriction enzyme site, as long as the restriction enzyme site recognizes a palindromic sequence. The adapter (B) preferably comprises a restriction enzyme site that recognizes a rare gene sequence that hardly cleaves DNA of interest. Examples of the restriction enzyme site contained in the Y portion of the adapter (B) include the following EcoRI site and PacI site.

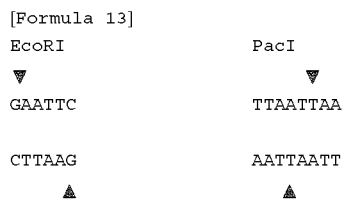

The cleavage ends generated as a result of the cleavage of the palindromic restriction enzyme sites $y_1$ and $y_2$ in the adapter (B) are all complementary to each other, and by ligation of such cleavage ends, there can be obtained a structure in which there are two identical or different unique sequences in the adapter (b) portion.

In addition, such a preferred adapter (B) has two identical restriction enzyme sites ($y_1$ and $y_2$) in the Y portion thereof. Thus, the adapter (B) is advantageous in that a circular DNA molecule, in which a sequence between the two restriction enzyme sites has not been eliminated after the second cleavage step, can be determined and eliminated as an "incomplete clone" on which the restriction enzyme treatment has not progressed well in the second cleavage step (FIG. 7).

Preferred examples of the sequence of the adapter (B) are shown in SEQ ID NO: 3 (forward direction chain) and SEQ ID NO: 4 (reverse direction chain).

When the adapter (A) comprising the palindromic restriction enzyme site X and the adapter (B) having the above described structure $Z_1$—Y—$Z_2$-A are used, individual steps in the first and third embodiments of the present invention are as follows.

Figure 5:
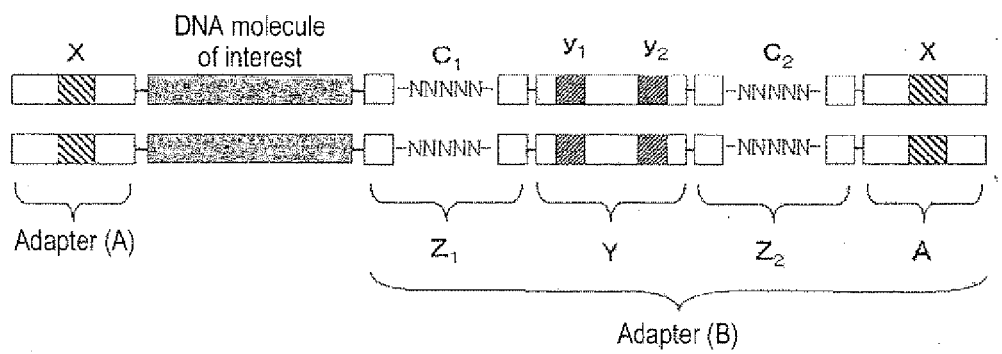
FIG. 5 schematically shows a DNA molecule after binding to adapters.

Step 1) is a step of binding an adapter (A) for a first circularization to one end of each DNA molecule of interest, and binding to the other end thereof an adapter (B) for a second circularization (FIG. 5)

Step 2) is a first cleavage step of cleaving the DNA molecule obtained in step 1) with the restriction enzyme (BamHI in FIG. 6) recognizing the palindromic restriction enzyme site X contained in the adapter (A) (A1 and B1 of FIG. 6).

Step 3) is a first circularization step of ligating both ends of the DNA molecule obtained in step 2) to circularize the DNA molecule (A2 and B2 of FIG. 6).

Step 4) is a step of eliminating an uncircularized linear DNA molecule in step 3).

Step 5) is a second cleavage step of cleaving the circular DNA molecule obtained in step 3) and step 4) with the restriction enzyme (EcoRI in FIG. 6) recognizing the palindromic restriction enzyme sites $y_1$ and $y_2$ in the adapter (b) (A3 and B3 of FIG. 6).

Step 6) is a second circularization step of ligating both ends of the DNA molecule obtained in step 5) to circularize the DNA molecule (A4, B4-1, B4-2, B4-3 and B4-4 of FIG. 6). By this step, there can be obtained a structure in which two identical or different unique sequences are contained in the adapter (b).

Step 7) included in the third embodiment of the present invention is a step of determining the sequence of the adapter (b) portion of the circular DNA molecule obtained in step 6) and then selecting only single-molecule circular DNA that is not derived from multiple-molecule circular DNA based on the results that two unique sequences contained in the adapter (b) are identical to or different from each other. After completion of step 6), the multiple-molecule circular DNA (B4-2, B4-3 and B4-4 of FIG. 6) and the single-molecule circular DNA derived from multiple-molecule circular DNA (B4-1 of FIG. 6) have a structure in which two different unique sequences are aligned in the adapter (b) (c-b, d-b, e-c, d-a, e-a and a-f in FIG. 6). On the other hand, the single-molecule circular DNA that is not derived from multiple-molecule circular DNA (A4 of FIG. 6) has a structure in which two identical unique sequences are aligned (a-a in FIG. 6). Accordingly, by selecting a molecule, in which two identical unique sequences are contained in an adapter (b) thereof, from the circular DNA molecules obtained in step 6), only the single-molecule circular DNA that is not derived from multiple-molecule circular DNA can be selected as an analysis target.

Moreover, when the restriction enzyme treatment had been successfully performed in the second cleavage step, the adapter (b) portion after completion of the second circularization step would have had a structure in which one restriction enzyme site is sandwiched between two unique sequences. On the other hand, when the restriction enzyme treatment had been performed incompletely, the DNA would have had a structure, in which a sequence between the restriction enzyme sites would not be eliminated, and two restriction enzyme sites would remain (FIG. 7). Accordingly, by determining the sequence of the adapter (b) portion, a clone with the latter structure can be distinguished as an incomplete clone and can be eliminated from analysis targets.

The Length of a Unique Sequence

The length of a unique sequence in an adapter (b) (that is "n" in the structure of an adapter having the above described structure $Z_1$—Y—$Z_2$-A or $Z_1$—Y—$Z'_2$-A) is not particularly limited, and it is preferably 1 to 40 nucleotides, more preferably 4 to 15 nucleotides, and even more preferably 5 to 10 nucleotides. As the number of nucleotides increases, the type of unique sequences also increases. As a result, the probability that different DNA molecules having the same adapter (b) portion (namely, having the same unique sequence) bind to one another to form multiple-molecule circular DNA in the first circularization step decreases.

For example, when a unique sequence has a length of 8 nucleotides, the type of the unique sequence (the type of the adapter (b)) will be $4^8$ (=65,536 types). In this case, the probability that single-molecule circular DNA derived from multiple-molecule circular DNA (for example, B4-1 of FIG. 6) after the second circularization step have two identical unique sequences is identical to the probability that different DNA molecules having the same adapter (b) portion bind to one another to form multiple-molecule circular DNA in the first circularization step, and it is 1/65536×1/65536=2.3×10e-10. In addition, multiple-molecule circular DNA (for example, B4-2, B4-3 and B4-4 of FIG. 6) after the second circularization step cannot be distinguished from single-molecule circular DNA that is not derived from multiple-molecule circular DNA (for example, A4 of FIG. 6), in a case in which identical unique sequences are aligned in both of the two adapter (b) portions, when it is circularization with two molecules. Accordingly, that probability is $1/65536^4$=5.4× 10e-20 (in the case of B4-2), $1/65536^3$=3.6×10e-15 (in the case of B4-3), or $1/65536^2$=2.3×10e-10 (in the case of B4-4). Moreover, when an adapter portion and a sequence flanking thereto are cut out and only the sequence of the thus cut portion is determined in mate-pair analysis and the like, the probability that all molecules of B4-2, B4-3 and B4-4 of FIG. 6 cannot be distinguished from the molecule of A4 of FIG. 6 is $1/65536^2$=2.3×10e-10.

These probabilities are considered to be sufficiently low. However, since the length of the unique sequence is not particularly limited, the possibility that multiple-molecule circular DNA or single-molecule circular DNA derived from the multiple-molecule circular DNA can be incorrectly determined to be single-molecule circular DNA that is not derived from multiple-molecule circular DNA can bring as close as possible to 0 (zero) by increasing the length such as a length of 9 nucleotides, 10 nucleotides, 11 nucleotides, or more.

Accordingly, by determining the sequence of the adapter (b) portion comprising unique sequences after the second circularization step, whether the DNA is single-molecule circular DNA that is not derived from multiple-molecule circular DNA, or multiple-molecule circular DNA, or single-molecule circular DNA derived from the multiple-molecule circular DNA, can be completely determined.

A Fourth Embodiment of the Present Invention

In a fourth embodiment, the present invention provides an adapter (B) preferably used in the methods of the first to third embodiments of the present invention, namely, an adapter for producing a circular DNA consisting of a double stranded DNA, wherein the two DNA strands are complementary to each other, having the following structure $Z_1$—Y—$Z_2$-A or $Z_1$—Y—$Z'_2$-A, wherein the adapter enables to select only single-molecule circular DNA that is not derived from multiple-molecule circular DNA from a group of the circular DNA molecules produced using the adapter:

[Formula 14]

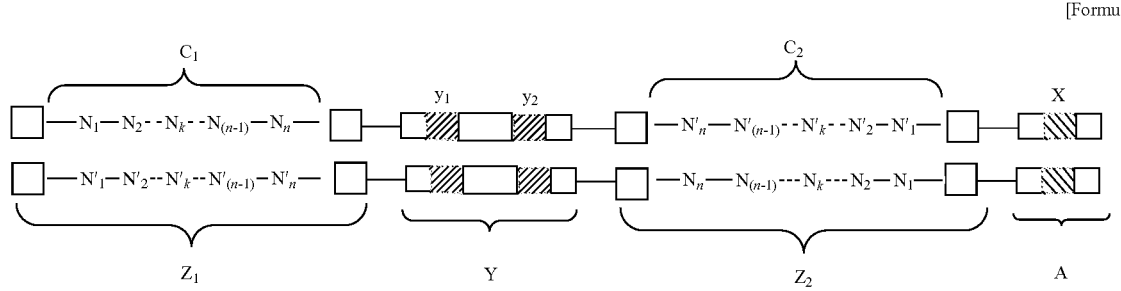

wherein

A represents a double-stranded DNA comprising the palindromic restriction enzyme site X;

Y represents a double-stranded DNA comprising palindromic restriction enzyme sites $y_1$ and $y_2$;

$y_1$ and $y_2$ are identical to each other and generate a cleavage end having a sequence different from X and being not complementary to a cleavage end generated as a result of the cleavage of X;

$Z_1$ and $Z_2$ are double-stranded DNA sequences comprising unique sequences $C_1$ and $C_2$, which are different depending on each adapter, wherein $C_1$ and $C_2$ are identical in sequence and reversely oriented to each other;

n represents an integer of more than 1 and less than 40;

$N_1$ to $N_n$, which may be the same or different, each represent a deoxyribonucleotide selected from the group consisting of dAMP, dCMP, dGMP and dTMP; and $N'_1$ to $N''_n$ represent the following deoxyribonucleotides respectively corresponding to the $N_1$ to $N_n$,

TABLE 4

| $N_k$ | $N'_k$ |
|---|---|
| dAMP | dTMP |
| dCMP | dGMP |
| dGMP | dCMP |
| dTMP | dAMP | wherein k represents an integer from 1 to n, or

[Formula 15]

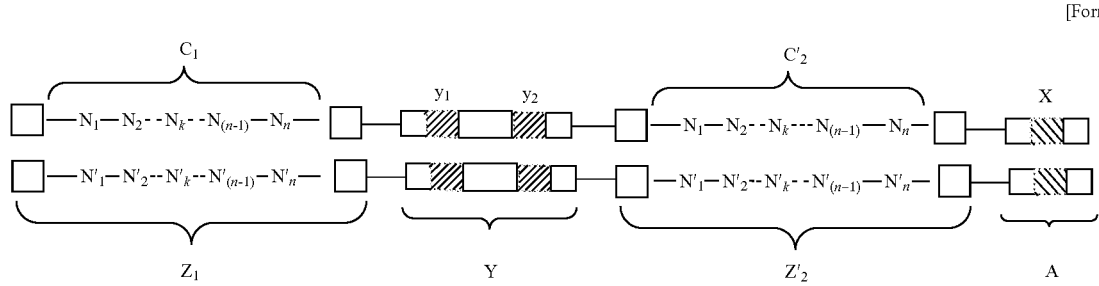

wherein
$Z_1$ and $Z'_2$ are double-stranded DNA sequences comprising unique sequences $C_1$ and $C'_2$, which are different depending on each adapter, wherein $C_1$ and $C_2$ are identical in sequence and oriented in the same direction; and
A, X, Y, $y_1$, $y_2$, n, $N_1$ to $N_n$, $N'_1$ to $N'_n$, and k have the same definitions as those the above described structure $Z_1$—Y—$Z_2$-A.

In both of the above structures $Z_1$—Y—$Z_2$-A and $Z_1$—Y—$Z'_2$-A, to 40, preferably 4 to 15, and more preferably 5 to 10. However, even when n is more than 40, the method of the present invention can be carried out.

As with the above described first and third embodiments, in the fourth embodiment of the present invention, examples of the restriction enzyme site X contained in the A portion include a BamHI site, an NotI site, and a BclI site, and examples of the restriction enzyme sites $y_1$ and $y_2$ contained in the Y portion include an EcoRI site and a PacI site.

Method for Producing Adapter (b)

Figure 8:
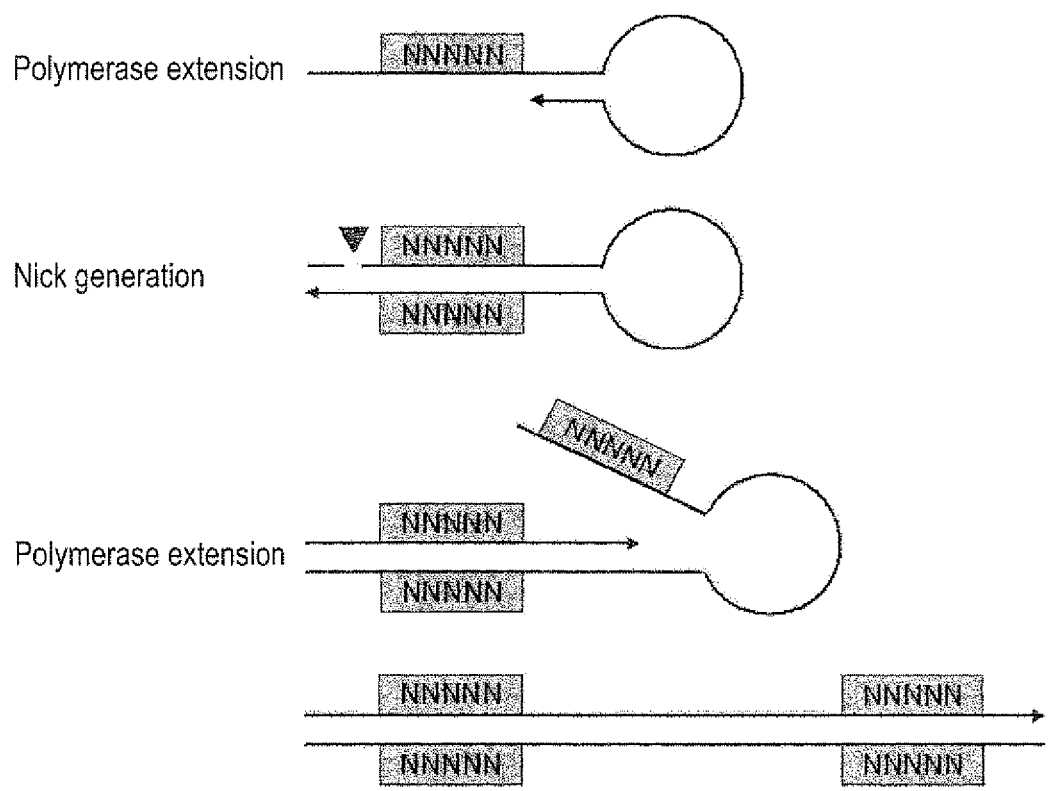
FIG. 8 schematically shows an example of a method for producing an adapter (b). In the figure, NNNNN indicates a unique sequence.

The adapter (b) having two identical unique sequences, which is preferably used in the above described first to third embodiments of the present invention and which includes, as a representative example, the structure $Z_1$—Y—$Z_2$ or $Z_1$—Y—$Z'_2$ in the adapter in the above described fourth embodiment, can be produced, for example, by performing 3 stages of reactions, namely, polymerase extension, nick production and polymerase extension, using nucleic acids having a hairpin structure (FIG. 8). However, the production method is not limited thereto, and a desired adapter (b) can be produced, for example, by sequence synthesis or the like.

A Fifth Embodiment of the Present Invention

In a fifth embodiment, the present invention provides a kit for producing a circular DNA which comprises adapter (A) and adapter (B) preferably used in the methods of the above described first to third embodiments of the present invention, wherein the kit enables to select only single-molecule circular DNA that is not derived from multiple-molecule circular DNA from a group of circular DNA molecules produced using the kit. That is to say, the fifth embodiment of the present invention provides a kit for producing a circular DNA, comprising an adapter (A) consisting of double-stranded DNA comprising a restriction enzyme site identical to the restriction enzyme site X according to the above described fourth embodiment, and an adapter (B) according to the above described fourth embodiment.

The kit for producing a circular DNA of the present invention comprises adapter (A) and adapter (B), and it allows these adapters to bind to both ends of a DNA molecule of interest and carries out the two-stage circularization method according to the first or third embodiment of the present invention, so as to obtain circular DNA having a specific structure capable of distinguishing single-molecule circular DNA that is not derived from multiple-molecule circular DNA, from multiple-molecule circular DNA and also from single-molecule circular DNA derived from the multiple-molecule circular DNA, and so as to select only the single-molecule circular DNA that is not derived from multiple-molecule circular DNA.

A Sixth Embodiment of the Present Invention

The sixth embodiment of the present invention is a method for producing a cDNA library, comprising using the two-step circularization method according to any of the first to third embodiments of the present invention.

By applying the method according to the first embodiment of the present invention to a library of linear cDNAs to determine the sequences of adapter (b) portions in the members of the library, there can be produced a cDNA library capable of selecting only the member that is single-molecule circular DNA that is not derived from multiple-molecule circular DNA. Accordingly, when gene analysis is carried out using such a cDNA library, for example, after the sequence of the library has been comprehensively read, only the data of single-molecule circular DNA that is not derived from multiple-molecule circular DNA can be selected as an analysis target.

By applying the method according to the second or third embodiment of the present invention to a library consisting of linear cDNAs, a cDNA library consisting only of a single-molecule circular DNA that is not derived from multiple-molecule circular DNA can be produced.

A Seventh Embodiment of the Present Invention

The seventh embodiment of the present invention is a method for identifying a gene by subjecting a circular DNA molecule to a mate-pair method, the method comprising the following steps:
1) a step of reading nucleotide sequences each consisting of 15 nucleotides or more and 600 nucleotides or less that are flanking to both sides of an adapter (B), in the group of circular DNA molecules produced by the method in the first embodiment of the present invention, the single-molecule circular DNA that is not derived from multiple-molecule circular DNA produced by the method in the second embodiment of the present invention, or the single-molecule circular DNA that is not derived from multiple-molecule circular DNA, which is selected by the method in the third, embodiment of the present invention, wherein when the group of circular DNA molecules produced by the method in the first embodiment of the present invention is used, the method further comprises a step of selecting only the single-molecule circular DNA that is not derived from multiple-molecule circular DNA by determining the sequence of the adapter (b) portion, before the step, or at the same time as the step, or after the step; and 2) a step of identifying a gene contained in the single-molecule circular DNA that is not derived from multiple-molecule circular DNA by comparing the nucleotide sequences read in step 1) with the sequences of both ends of a known gene.

Step 1) in the method of the seventh embodiment of the present invention is a step of reading nucleotide sequences, each consisting of 15 to 600 nucleotides, flanking to both sides of the adapter (B) in the circular DNA molecule obtained using the method according to the first to third embodiments of the present invention. The nucleotide sequence to be read consists of preferably 15 to 100 nucleotides, and more preferably 25 to 35 nucleotides. However, the method of the present invention can also be carried out by reading a nucleotide sequence consisting of 600 or more nucleotides. The nucleotide sequence can be read by a method well known to a person skilled in the art, for example, using a sequencer.

In the step 1), the case of determining the sequence of the adapter (b) portion "at the same time as the step" is, for example, a case in which, in a sequencing reaction of reading nucleotide sequences flanking to both sides of the adapter (B), the sequence starts to be read from outside of the nucleotide sequences flanking thereto towards the adapter (B), and the sequence is continuously read into inside of the adapter (B), so that even the sequence of the adapter (b) portion can be determined simultaneously.

Otherwise, there is also a case in which the same sample as described above is divided into multiple samples used for reading the sequence outside of the adapter (B) and for reading the sequence of the adapter (b) portion, and these samples are simultaneously subjected to a sequencing reaction, so that individual sequence data is obtained.

In all of these cases, only the data of a sample in which two unique sequences in the adapter (b) portion are identical to each other (namely, single-molecule circular DNA that is not derived from multiple-molecule circular DNA) can be selected as an analysis target.

Step 2) in the method of the seventh embodiment of the present invention is a step of identifying a gene contained in the circular DNA molecule by comparing the read nucleotide sequences with the sequences of both ends of a known gene. When the read nucleotide sequences, which correspond to the sequences on both ends of a DNA molecule of interest, can be confirmed to be identical to the sequences of both ends of a known gene, then the DNA molecule of interest is identified to be the known gene.

An Eighth Embodiment of the Present Invention

The eighth embodiment of the present invention is a method for detecting a fusion gene by subjecting a circular DNA molecule to a mate-pair method, the method comprising the following steps:

1) a step of reading nucleotide sequences each consisting of 15 nucleotides or more and 600 nucleotides or less that are flanking to both sides of an adapter (B), in the group of circular DNA molecules produced by the method in the first embodiment of the present invention, the single-molecule circular DNA that is not derived from multiple-molecule circular DNA produced by the method in the second embodiment of the present invention, or the single-molecule circular DNA that is not derived from multiple-molecule circular DNA, which is selected by the method in the third embodiment of the present invention, wherein when the group of circular DNA molecules produced by the method in the first embodiment of the present invention is used, the method further comprises a step of selecting only the single-molecule circular DNA that is not derived from multiple-molecule circular DNA by determining the sequence of the adapter (b) portion, before the step, or at the same time as the step, or after the step; and 2) a step of comparing the nucleotide sequences read in step 1) with the sequences of both ends of a known gene, wherein when the genes of both ends correspond to known different genes, the gene comprised in single-molecule circular DNA that is not derived from multiple-molecule circular DNA is identified to be a fusion gene.

Step 1) in the method of the eighth embodiment of the present invention is a step of reading nucleotide sequences, each consisting of 15 to 600 nucleotides, flanking to both sides of an adapter (B) in a circular DNA molecule obtained by using the method according to the first to third embodiments of the present invention. The nucleotide sequence to be read consists of preferably 15 to 100 nucleotides, and more preferably 25 to 35 nucleotides. However, the method of the present invention can also be carried out by reading a nucleotide sequence consisting of 600 or more nucleotides. The nucleotide sequence can be read by a method well known to a person skilled in the art, for example, using a sequencer.

In the step 1), the case of determining the sequence of the adapter (b) portion "at the same time as the step" is similar to the case of the above described seventh embodiment.

Step 2) in the method of the eighth embodiment of the present invention is a step of comparing the read nucleotide sequences with the sequences of both ends of a known gene. Herein, when the genes of both ends correspond to known different genes, the gene comprised in the circular DNA molecule is identified to be a fusion gene. That is to say, when a portion, which corresponds to one end of the read nucleotide sequences corresponding to the sequences on both ends of a DNA molecule of interest, is identical to one end of a known gene, and when a portion corresponding to the other end is identical to one end of another known gene, the DNA molecule of interest is identified to be a fusion gene consisting of two known genes.

As an example, when the sequences of both sides flanking to both sides of the adapter (B) correspond to both ends of a known fusion gene, the DNA of interest is detected to be the known fusion gene. When the relationship between the expression of the known fusion gene and a disease has been known, it is possible to detect a disease characterized by the expression of the fusion gene detected by the aforementioned method, using the fusion gene as a marker.

As another example, when the sequences flanking to both sides of the adapter (B) correspond to the terminal sequences of different genes and do not correspond to both ends of a known fusion gene, the gene contained in the circular DNA molecule is identified to be a novel fusion gene. The novel fusion gene detected by the aforementioned method can be used in drug discovery screening.

EXAMPLES

Specific methods of allowing adapters to bind to both ends of a DNA molecule of interest (the left and right ends of a DNA molecule of interest) will be described in the following.

Example 1

Figure 9:
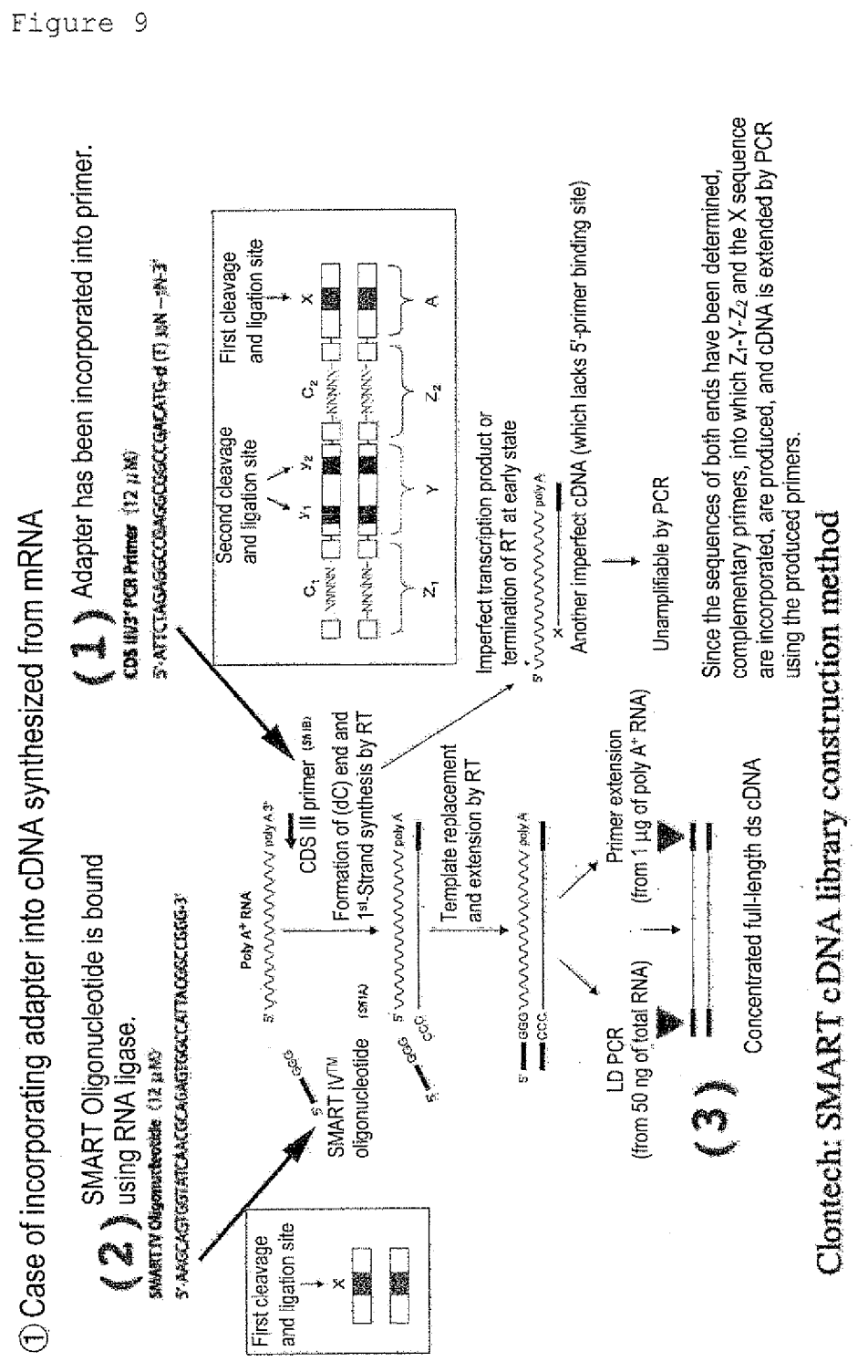

Application of the Method of the Present Invention to the Discovery of a Fusion Gene, in which cDNA Synthesized from mRNA is Used When a cDNA library is synthesized from mRNA, in the most common method (Clontech SMART cDNA method) among the currently used methods, complementary strand DNA is first synthesized with reverse transcriptase, using oligonucleotide (1) having a poly T sequence complementary to a poly A site at the 3'-terminus of mRNA, as shown in FIG. 9. After completion of the synthesis, a specific oligonucleotide sequence (2) is incorporated at the 5'-terminus of mRNA, as shown in FIG. 9. Subsequently, DNA is synthesized from an oligonucleotide complementary to this specific sequence, or a cDNA library is produced by PCR.

Case in which the Adapters of the Present Invention are Incorporated into cDNA at the Same Time with the cDNA Synthesis In this case, the adapter (B) has been introduced into the oligonucleotide (1) sequence having a poly T sequence complementary to a poly A site at the 3'-terminus of mRNA, and the adapter (A) has been added to the oligonucleotide (2) sequence. Thus, when a cDNA library is synthesized, it automatically becomes the basic structure of the present invention. It is not necessary to bind new sequences to the right and left ends, and the routine can directly proceed to the next step (FIG. 9). By this method, when the cDNA library is further amplified by PCR, when it is directly amplified, a specific unique sequence must be amplified. Hence, in order to maintain the diversity of unique sequences, the following procedures are carried out. That is, amplification is carried out using, for example, a 5' phosphate group-added primer as an upstream primer, and a primer containing the unique sequence as a downstream primer, and after completion of the PCR, a strand into which the phosphate group primer has been incorporated is digested with λ exonuclease. Thereafter, primer extension is carried out again from the upstream primer, so as to produce a cDNA library in which the diversity of unique sequences can be maintained. However, in the case of the adapter binding method, this process is not necessary. In order to introduce the adapter of the present invention after modification, such as fragmentation of the library, the subsequent adapter binding method is carried out.

Case in which the Adapter of the Present Invention is Incorporated into cDNA after Ordinary cDNA Synthesis When a cDNA library is produced, it is possible that a restriction enzyme site has been introduced into each of the 3'-terminus and 5'-terminus thereof, as shown in FIG. 9(3). As a restriction enzyme site used in this case, either an ordinary palindromic restriction enzyme site, or a non-palindromic restriction enzyme site for distinguishing the 3'-terminus and 5'-terminus, can be used. Moreover, in order to ensure adapter binding, the adapter can also be bound to an end with an A-protruding nucleotide, instead of a blunt end. In order to introduce the adapter of the present invention after modification of the library, this method is desirable.

Example 2

Figure 10:
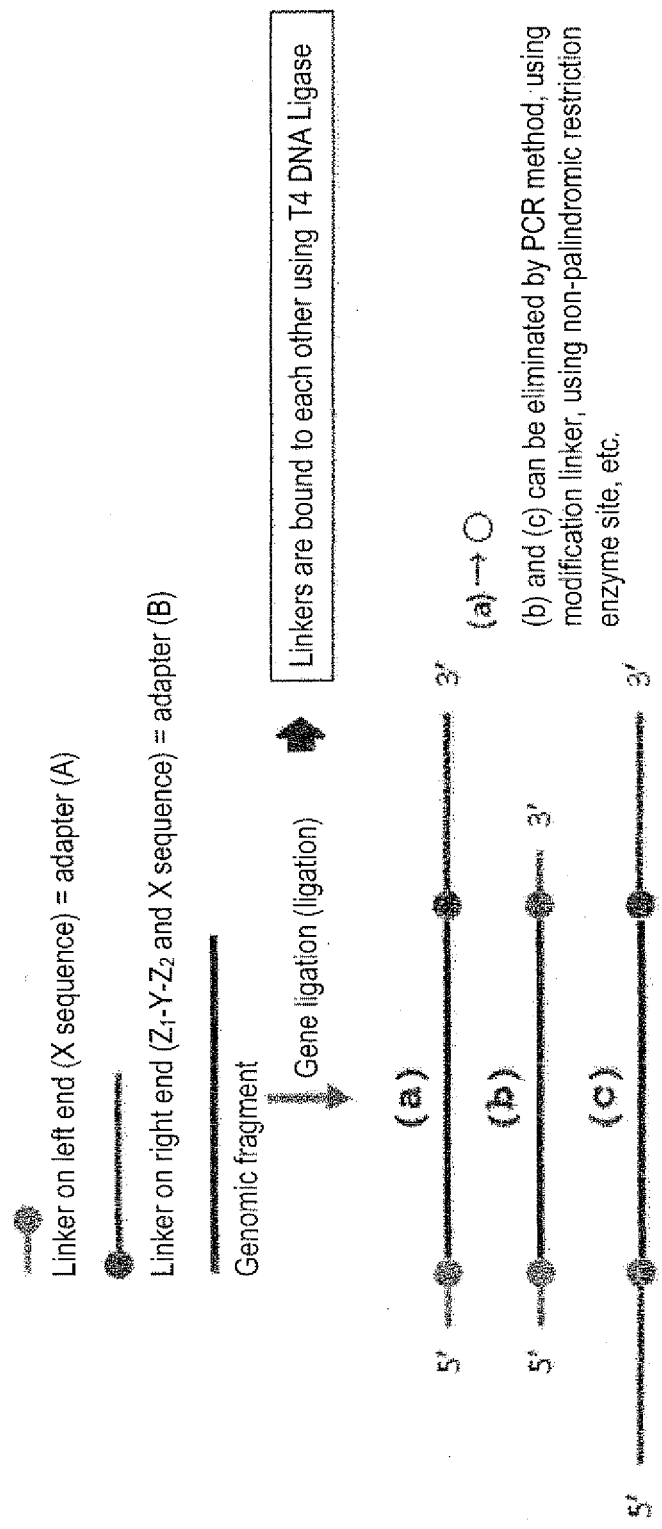
FIG. 10 is a schematic view showing application of the method of the present invention to a genomic library. Differing from cDNA, a genomic fragment cannot distinguish the left and right sides of a DNA fragment. Accordingly, as shown in this figure, only a product (a), which is prepared by binding a linker on the left end to a linker on the right end so that the two linkers are appropriately ligated to each other, can be selected by a PCR method, or by using modification linkers, or by using non-palindromic sequences as a restriction enzyme site X sequences on both ends, etc.

Application of the Method of the Present Invention to Genomic Analysis by Mate-Pair Method When genome is targeted, the situation is different from the case of a cDNA library. Differing from cDNA, a genomic fragment cannot distinguish the left and right sides of a DNA fragment. Accordingly, as shown in FIG. 10, only the product (a) in FIG. 10, namely, a product prepared by binding the adapter on the left end to the adapter on the right end so that the two adapters are appropriately ligated, can be selected by a PCR method or a method using a modification linker, or by using non-palindromic sequences as a restriction enzyme site X on both ends, or a method of establishing a plurality of restriction enzyme sites at the same site, using restriction enzyme (BstXI, etc.) containing an N region, etc.

For example, when the OCR method is applied, detection can be carried out using a primer reacting with either a linker (adapter) region. When the method using a modification linker (adapter) is applied, for example, a left-end linker has previously been modified with biotin, and a right-end linker has previously been modified with DIG (digoxigenin). Thereafter, positive selection of the biotin-modified linker with streptavidin and positive selection of the DIG-modified linker with an anti-DIG antibody are carried out, so that a fragment having both the left-end linker and the right-end linker can be concentrated. Substances used for modification are not limited to biotin and DIG, and it may also be adequate when the left-end linker and the right-end linker are modified with different modification substances. The case of using a restriction enzyme site with a non-palindromic sequence will be described in detail below.

Adapters (A) and (B) Added to Both Ends of a DNA Molecule

Basically, the following method is adopted to add adapters (A) and (B) to both ends of a DNA molecule. At first, to a group of a plurality of DNAs, the concentration of which has been almost determined depending on the number of DNA molecules of interest, an adapter (A) is first allowed to bind. In this case, the amount of the adapter (A) added is set to be smaller than the amount of the target DNA molecules. However, stoichiometrically, the number of the adapters (A) may be the same as the number of the target DNA molecules, or one nucleotide protrusion may be enzymatically produced on a DNA fragment and a complementary adapter may be allowed to bind thereto. Especially, in this case, the concentration of the adapter may be excessive. Thereby, the adapter (A) is allowed to bind to the end of the DNA molecule. Subsequently, an adapter (B) is allowed to bind.

In the present invention, as shown in (a) of FIG. 10, it is necessary to produce a molecule in which the adapter (A) binds to one end thereof and the adapter (B) binds to the other end. Herein, as shown in (b) or (c) of FIG. 10, it is necessary to eliminate a DNA molecule to which only the adapter (A) binds ((b) of FIG. 10) and a DNA molecule to which only the adapter (B) binds ((c) of FIG. 10). The methods therefor will be described below.

Case of Using a Non-Palindromic Sequence to a Restriction Enzyme Site X of the Adapter (A)

For example, adaptor "A1" for generating the cleavage end W1 is used as adapter (A), and adapter "A2" for generating the cleavage end W2 is used as adapter (A) contained in adapter (B). Herein, the cleavage ends W1 and w2 are complementary to each other, but two W1 or two W2 are not complementary to each other. That is to say, sequences are designed or selected such that ligation can be carried out only between adapters "A1" and "A2."

In the case of a molecule of type (a) of FIG. 10, a first circularization, a second cleavage, and a second circularization are carried out without problems, and as a result, circularized DNA of interest is produced without problems. On the other hand, in the case of molecules of type (b) (both ends are "A1") and of type (c) (both ends are "A2") of FIG. 10, since they cannot be circularized by themselves, they are eliminated as linear molecules after completion of the first circularization step.

Moreover, either one end cannot bind between the molecule of type (a) (wherein one end is "A1", and the other end is "A2") and the molecule of type (b), and between the molecule of type (a) and the molecule of type (c), and as a result, the first circularization cannot take place. Accordingly, these molecules are also eliminated as linear molecules.

The first circularization can take place between the molecule of type (b) and the molecule of type (c), and as a result, multiple-molecule circularized DNA is formed. However, as described later, the probability that the molecule of type (b) and the molecule of type (c), which had been separated by the second cleavage step, are rebound to each other is substantially 0 (zero). Furthermore, single-molecule DNAs, in which the molecule of type (b) and the molecule of type (c), which had been separated by the second cleavage step, are each self-circularized, have a structure in which two different unique sequences are aligned. Accordingly, it is possible to distinguish and eliminate these DNAs.

Case of Using a Palindromic Sequence to a Restriction Enzyme Site X of the Adapter (A)

In the case of molecules of type (a) of FIG. 10, a first circularization, a second cleavage, and a second circularization are carried out without problems, and as a result, circularized DNA of interest is produced without problems. On the other hand, in the case of molecules of type (b) of FIG. 10, the first circularization is possible by themselves. However, since this molecule does not have an adapter (b) portion, a second cleavage is not carried out, and it remains as circularized DNA and cannot be eliminated. As an example of a method of preventing this, there is a "BstXI method" as described below.

In addition, in the case of a molecule of type (c) of FIG. 10, it can carry out a first circularization by itself. However, when the molecule is subjected to second cleavage and second circularization steps, it has a structure in which two different unique sequences are aligned. Accordingly, it is possible to distinguish and eliminate this molecule.

When a first circularization takes place between the molecule of type (a) and the molecule of type (b), even after completion of a second circularization, the generated DNA cannot be distinguished from single-molecule circular DNA that is not derived from multiple-molecule circular DNA because of its structure. However, since the DNA comprises a binding site between adapters (A) that is not contained in adapter (B), it can converted to a linear molecule, for example, according to the following "BstXI method," and it can be then eliminated.

When a first circularization takes place between the molecule of type (a) and the molecule of type (c), three linear molecules are generated by the second cleavage. The probability that these molecules are rebound to return to an original condition is substantially 0 (zero), and all of circular DNAs generated as a result of the self-circularization of such linear molecules in the second circularization step have a structure in which two different unique sequences are aligned. Accordingly, it is possible to distinguish and eliminate these circular DNAs.

The first circularization can take place between the molecule of type (b) and the molecule of type (c), and as a result, multiple-molecule circularized DNA can be formed. However, as described later, the probability that the molecule of type (b) and the molecule of type (c), which have been separated by the second cleavage step, are rebound to each other is substantially 0 (zero), and single-molecule DNAs generated as a result of the self-circularization of the molecule of type (b) and the molecule of type (c), which had been separated by the second cleavage step, have a structure in which two different unique sequences are aligned. Accordingly, it is possible to distinguish and eliminate these DNAs.

BstXI Method

In a case in which adapters (A) are added to both ends, both ends are ligated at a first stage. However, since cleavage does not take place at a second stage, it remains as circular DNA. As a method of solving this problem, BstXI is added to the outside of the adapter (A) comprising the restriction enzyme site, for example. Specifically, into the following restriction enzyme BstXI site, a BamHI site is incorporated, so that CCANNNNNNTGG is converted to CCAGGATCCTGG, for example.

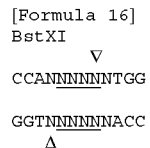

[Formula 16]

That is to say, in this method, the restriction enzyme site of each of the adapter (A), and the adapter (A) contained in the adapter (B), is set to be a BamHI site, for example. Then, only in the case of the adapter (A), the sequence outside the BamHI site is set to be a BstXI recognition sequence, for example. That is, the sequence of the adapter (A) is set to be CCAGGATCCTGG. On the other hand, the adapter (A) contained in the adapter (B) comprises a BamHI site but does not comprise a BstXI recognition sequence, so that it cannot be cleaved with BstXI. As a result, when the only adapters (A) bind to both ends and are then associated with each other, circularization can be opened by cleaving with BstXI and can be then eliminated. Of course, when the adapter (A) binds to the adapter (B), since the adapter (B) does not have a BstXI recognition sequence, it cannot be cleaved with BstXI.

According to the above described method, the method of the present invention can be applied even to a genomic DNA fragment that cannot distinguish between upstream and downstream, differing from cDNA, so that single-molecule circular DNA that is not derived from multiple-molecule circular DNA can be produced and/or selected, and so that the accuracy of mate-pair analysis can be significantly improved.

Example 3

The Possibility of Rebinding of the Same DNA Molecules in Multiple-Molecule Circular DNA The possibility that DNA molecules separated by the second cleavage step are re-associated can be fully ignored, stochastically. The grounds will be described below.

In order to stochastically assume the possibility that one DNA molecule generated by the cleavage of multiple-molecule circular DNA by the second cleavage step is re-associated with the other DNA molecule to which the one DNA molecule has bound before the cleavage, such possibility is estimated in the following two cases: (1) a case in which the possibility is assumed from the volume of a DNA molecule and the amount (volume) of a reaction solution; and (2) a case in which the possibility is assumed from the number of molecules in the reaction solution.

(1) The Case in which the Possibility is Assumed from the Volume of a DNA Molecule and the Amount (Volume) of a Reaction Solution First, a single DNA molecule is presumed to be a sphere and its volume is estimated. Then, the possibility that molecules that have once been separated in a reaction system are associated as spheres in a solution is estimated.

The length of one nucleotide: 0.34 nm ($0.34 \times 10e-9$ m=$3.4 \times 10e-8$ mm), the length of a 3-kbp (3000 bp) plasmid: $1 \times 10e-4$ mm, the volume of a DNA molecule assumed to be a sphere: $4/3 \times 3.14 \times (1 \times 10e-4) \times (1 \times 10e-4) \times (1 \times 10e-4)$ mm$^3$=$4 \times 10e-12$ mm$^3$, and When the volume of a single molecule is assumed to be $4 \times 10e-12$ mm$^3$, the number of DNA molecules as spheres in 100 μL is presumed to be 100 mm$^3$/$4 \times 10e-12$ mm$^3$=$2.5 \times 10e13$ molecules.

Accordingly, when the reaction system is homogeneous, the possibility that a sphere is associated with another equivalent sphere complementary thereto is extremely small ($(1/(2.5 \times 10e13))$=$4 \times 10e-14$).

(2) The Case in which the Possibility is Assumed from the Number of Molecules in the Reaction Solution On the other hand, the number of molecules is calculated as follows.

The molecular weight of a 3-kbp plasmid: $625 \times 3000$=$1.8 \times 10e6$, the mass of 1 mole of plasmid: 1 mol=$1.8 \times 10e6$ g=$1.8 \times 10e12$ μg, the molar number of 3 μg of plasmid: 3 μg/($1.8 \times 10e12$) μg=$3/1.8 \times 10e-12$ mol=$1.6 \times 10e-12$ mol, and the number of molecules of 3 μg of plasmid when the Avogadro's number is presumed to be $6 \times 10e23$: $1.6 \times 10e-12 \times 6 \times 10e23$=$1.6 \times 6 \times 10e11$=$1 \times 10e12$.

Accordingly, when 3 μg of plasmid is present in 100 μL of reaction system, for example, the possibility that one molecule separated in the second cleavage step is re-associated with the other molecule (namely, having the same unique sequence) is extremely small ($1/((1 \times 10e12)-1)$=$1 \times 10e-12$).

Accordingly, from these estimations, it can be concluded that the possibility that, after a plurality of DNAs have formed a ring and they have been then separated, identical DNA molecules before separation rebind to each other, is extremely low, and thus, it can be fully ignored.

INDUSTRIAL APPLICABILITY

Using the adapter and method of the present invention, the accuracy of gene analysis is significantly improved. Specifically, by using the adapters and methods of the present invention, it becomes possible to completely distinguish single-molecule circular DNA that is not derived from multiple-molecule circular DNA, from multiple-molecule circular DNA and also from single-molecule circular DNA derived from the multiple-molecule circular DNA, and at a probability of almost 100%, only the single-molecule circular DNA that is not derived from multiple-molecule circular DNA can be selected. As a result, unconventional high-accuracy mate-pair analysis becomes possible, and thus, the adapter and method of the present invention are provided as tools extremely useful for genomic analysis. In particular, by applying the method of the present invention to the production of a cDNA library, it is highly likely to discover a novel fusion gene. That is to say, by eliminating multiple-molecule circular DNA, which causes a problem in the mate-pair analysis, at the stage of sequence analysis, and by selecting only single-molecule circular DNA that is not derived from multiple-molecule circular DNA, it becomes possible to develop a novel diagnostic tool and/or method.

According to the present invention, a method for selecting only single-molecule circular DNA that is not derived from multiple-molecule circular DNA with regard to circularization of DNA, is provided. Accordingly, problems regarding contamination in gene analysis such as mate-pair analysis can be solved, and so that high-accuracy analysis becomes possible. Moreover, by applying the method of the present invention to detection and/or analysis of a fusion gene, high-accuracy analysis of a fusion gene becomes possible, and a useful diagnostic tool can be provided.

The invention claimed is:

1. A method for producing a single-molecule circular DNA that is not derived from multiple-molecule circular DNA, the method comprising the following steps:

A) a step of producing circular DNA molecules by the method of steps 1-6:

1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the adapter (b) side, such that the adapter (A) in the adapter (B) is located outside of the bond of the DNA molecule to the adapter (b), wherein the adapter (A) comprises a cleavage site generating a cleavage end non-specifically binding to all of the cleavage ends of the adapter (A), the adapter (b) comprises two unique sequences different depending on each adapter (b), wherein the two unique sequences are identical in sequence and oriented in the same direction or reversely to each other; and between the two unique sequences, the adapter (b) also comprises a cleavage site generating a cleavage end non-specifically binding to all of the cleavage ends of the adapters (b), wherein the cleavage site generates a cleavage end that is not cleaved upon cleaving the cleavage site of the adapter (A) and does not bind to the cleavage end of the adapter (A);

2) a first cleavage step of cleaving the DNA molecule obtained in step 1) at the cleavage site of the adapter (A);

3) a first circularization step of binding both ends of the DNA molecule obtained in step 2) to circularize the DNA molecule;

4) a step of eliminating an uncircularized linear DNA molecule in step 3);

5) a second cleavage step of cleaving the circular DNA molecule obtained in step 3) and step 4) at the cleavage site of the adapter (b); and 6) a second circularization step of binding both ends of the DNA molecule obtained in step 5) to circularize the DNA molecule, wherein the circular DNA molecule obtained in step 6) is determined to be single-molecule circular DNA that is not derived from multiple-molecule circular DNA, when two unique sequences contained in an adapter (b) portion are identical to each other as a result of determination of the sequence of the adapter (b) portion, and the circular DNA molecule obtained in step 6) is determined to be multiple-molecule circular DNA or single-molecule circular DNA derived from the multiple-molecule circular DNA, when the two unique sequences are different from each other; and B) a step of determining the sequence of an adapter (b) portion in the produced circular DNA molecules and selecting only single-molecule circular DNA that is not derived from multiple-molecule circular DNA, wherein the circular DNA molecule is determined to be single-molecule circular DNA that is not derived from multiple-molecule circular DNA, when two unique sequences contained in the adapter (b) portion are identical to each other, and the circular DNA molecule is determined to be multiple-molecule circular DNA or single-molecule circular DNA derived from the multiple-molecule circular DNA, when the two unique sequences are different from each other.

2. A method for selecting only single-molecule circular DNA that is not derived from multiple-molecule circular DNA in the production of circular DNA molecules, the method comprising the following steps:

1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the side of adapter (b), and the adapter (A) in adapter (B) is positioned outside of the bond of the DNA molecule to the adapter (b), wherein the adapter (A) comprises a cleavage site generating a cleavage end non-specifically binding to all of the cleavage ends of the adapter (A);

the adapter (b) comprises two unique sequences different depending on each adapter (b), wherein the two unique sequences are identical in sequence and oriented in the same direction or reversely to each other; and between the two unique sequences, the adapter (b) also comprises a cleavage site generating a cleavage end non-specifically binding to all of the cleavage ends of the adapter (b), wherein the cleavage site generates a cleavage end that is not cleaved upon cleaving the cleavage site of the adapter (A) and does not bind to the cleavage end of the adapter (A);

2) a first cleavage step of cleaving the DNA molecule obtained in step 1) at the cleavage site of the adapter (A);

3) a first circularization step of ligating both ends of the DNA molecule obtained in step 2) to circularize the DNA molecule;

4) a step of eliminating an uncircularized linear DNA molecule in step 3);

5) a second cleavage step of cleaving the circular DNA molecule obtained in step 3) and step 4) at the cleavage site of the adapter (b);

6) a second circularization step of ligating both ends of the DNA molecule obtained in step 5) to circularize the DNA molecule; and 7) a step of determining the sequence of the adapter (b) portion of the circular DNA molecule obtained in step 6) and then selecting only single-molecule circular DNA that is not derived from multiple-molecule circular DNA, wherein the circular DNA molecule is determined to be single-molecule circular DNA that is not derived from multiple-molecule circular DNA, when the two unique sequences contained in the adapter (b) portion are identical to each other, and the circular DNA molecule is determined to be multiple-molecule circular DNA or single-molecule circular DNA derived from the multiple-molecule circular DNA, when the two unique sequences are different from each other.

3. The method according to claim 2, wherein the adapter (b) comprises two cleavage sites generating a cleavage end non-specifically binding to all of the cleavage ends of the adapter (b) between the two unique sequences.

4. The method according to claim 2, wherein the adapter (A) consists of two DNA strands complementary to each other comprising a palindromic restriction enzyme site X, and the adapter (B) consists of two DNA strands complementary to each other having the following structure $Z_1$—Y—$Z_2$-A or $Z_1$—Y—$Z'_2$-A:

[Formula 3]

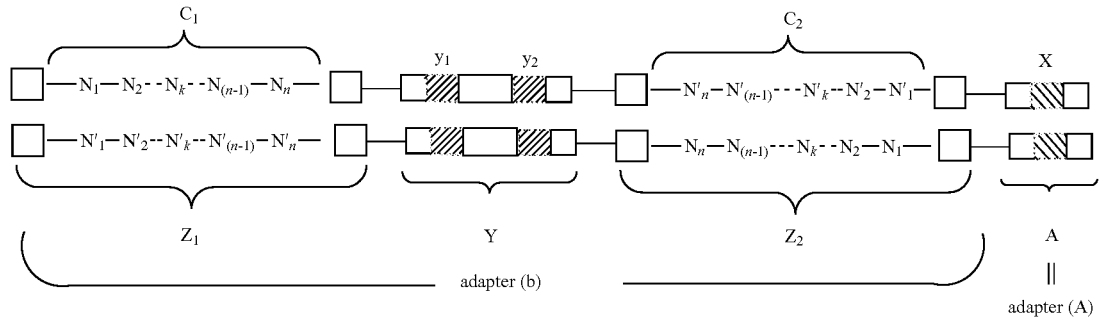

wherein
A represents a double-stranded DNA comprising the palindromic restriction enzyme site X, which corresponds to the adapter (A);
$Z_1$—Y—$Z_2$ corresponds to the adapter (b) in claim 2;
Y represents a double-stranded DNA comprising palindromic restriction enzyme sites $y_1$ and $y_2$;
$y_1$ and $y_2$ are identical to each other and generate a cleavage end having a sequence different from X and being not complementary to a cleavage end generated as a result of the cleavage of X;
$Z_1$ and $Z_2$ are double-stranded DNA sequences comprising unique sequences $C_1$ and $C_2$, which are different depending on each adapter, wherein $C_1$ and $C_2$ are identical in sequence and reversely oriented to each other;

n represents an integer of more than 1 and less than 40;
$N_1$ to $N_n$, which may be the same or different, each represent a deoxyribonucleotide selected from the group consisting of dAMP, dCMP, dGMP and dTMP; and
$N'_1$ to $N'_n$ represent the following deoxyribonucleotides respectively corresponding to the $N_1$ to $N_n$,

TABLE 2

| $N_k$ | $N'_k$ |
|-------|--------|
| dAMP  | dTMP   |
| dCMP  | dGMP   |
| dGMP  | dCMP   |
| dTMP  | dAMP   | wherein k represents an integer from 1 to n, or

[Formula 4]

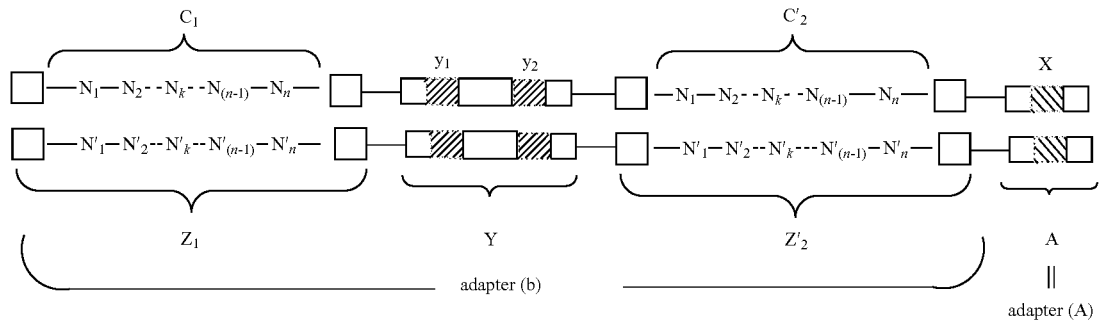

wherein
$Z_1$—Y—$Z'_2$ corresponds to the adapter (b) in claim 2;
$Z_1$ and $Z'_2$ are double-stranded DNA sequences comprising unique sequences $C_1$ and $C'_2$, which are different depending on each adapter, wherein $C_1$ and $C'_2$ are identical in sequence and oriented in the same direction; and
A, X, Y, $y_1$, $y_2$, n, $N_1$ to $N_n$, $N'_1$ to $N'_n$, and k have the same definitions as those in the above described structure $Z_1$—Y—$Z_2$-A.

5. A method for producing a cDNA library consisting only of single-molecule circular DNA that is not derived from multiple-molecule circular DNA, comprising using the method according to claim 1.

* * * * *

SEQUENCE LISTING

<160> NUMBER OF SEQ ID NOS: 6

<210> SEQ ID NO 1
<211> LENGTH: 16
<212> TYPE: DNA
<213> ORGANISM: Artificial
<220> FEATURE:
<223> OTHER INFORMATION: one strand of adaptor (A)

<400> SEQUENCE: 1
gcttagtgat cagcag                                                    16

<210> SEQ ID NO 2
<211> LENGTH: 20
<212> TYPE: DNA
<213> ORGANISM: Artificial
<220> FEATURE:
<223> OTHER INFORMATION: the other strand of adaptor (A)

<400> SEQUENCE: 2
aaaactgctg atcactaagc                                                20

```
<210> SEQ ID NO 3
<211> LENGTH: 89
<212> TYPE: DNA
<213> ORGANISM: Artificial
<220> FEATURE:
<223> OTHER INFORMATION: one strand of adaptor (B)
<220> FEATURE:
<221> NAME/KEY: misc_feature
<222> LOCATION: (18)..(23)
<223> OTHER INFORMATION: n is a, c, g, or t
<220> FEATURE:
<221> NAME/KEY: misc_feature
<222> LOCATION: (70)..(75)
<223> OTHER INFORMATION: n is a, c, g, or t

<400> SEQUENCE: 3
cctgctgtgg tacattcnnn nnngaattcc tgccttgccc ggcagtggaa gcgggcaagg    60
caggaattcn nnnnntgatc accttggat                                     89

<210> SEQ ID NO 4
<211> LENGTH: 85
<212> TYPE: DNA
<213> ORGANISM: Artificial
<220> FEATURE:
<223> OTHER INFORMATION: the other strand of adaptor (B)
<220> FEATURE:
<221> NAME/KEY: misc_feature
<222> LOCATION: (15)..(20)
<223> OTHER INFORMATION: n is a, c, g, or t
<220> FEATURE:
<221> NAME/KEY: misc_feature
<222> LOCATION: (67)..(72)
<223> OTHER INFORMATION: n is a, c, g, or t

<400> SEQUENCE: 4
atccaaggtg atcannnnnn gaattcctgc cttgcccgct ccactgccg ggcaaggcag    60 gaattcnnnn nngaatgtac cacag                                         85

<210> SEQ ID NO 5
<211> LENGTH: 39
<212> TYPE: DNA
<213> ORGANISM: Artificial
<220> FEATURE:
<223> OTHER INFORMATION: SMART IV oligonucleotide

<400> SEQUENCE: 5
aagcagtggt atcaacgcag agtggccatt acggccggg                          39

<210> SEQ ID NO 6
<211> LENGTH: 58
<212> TYPE: DNA
<213> ORGANISM: Artificial
<220> FEATURE:
<223> OTHER INFORMATION: CDS III/3' PCR primer
<220> FEATURE:
<221> NAME/KEY: misc_feature
<222> LOCATION: (58)..(58)
<223> OTHER INFORMATION: n is a, c, g, or t

<400> SEQUENCE: 6
attctagagg ccgaggcggc cgacatgttt tttttttttt tttttttttt tttttttn    58
```